(12) United States Patent
Meulewaeter

(10) Patent No.: US 10,174,335 B2
(45) Date of Patent: Jan. 8, 2019

(54) COTTON FIBERS WITH INCREASED GLUCOSAMINE CONTENT

(71) Applicant: Bayer CropScience NV, Diegem (BE)

(72) Inventor: Frank Meulewaeter, Merelbeke (BE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/122,485

(22) PCT Filed: Mar. 18, 2015

(86) PCT No.: PCT/EP2015/055603
§ 371 (c)(1),
(2) Date: Aug. 30, 2016

(87) PCT Pub. No.: WO2015/140191
PCT Pub. Date: Sep. 24, 2015

(65) Prior Publication Data
US 2017/0073698 A1    Mar. 16, 2017

(30) Foreign Application Priority Data

Mar. 21, 2014 (EP) .................................. 14161153

(51) Int. Cl.
*C12N 15/82* (2006.01)
*C12N 9/10* (2006.01)
*D02G 3/02* (2006.01)

(52) U.S. Cl.
CPC ....... *C12N 15/8246* (2013.01); *C12N 9/1096* (2013.01); *C12N 15/8223* (2013.01); *C12Y 206/01016* (2013.01); *D02G 3/02* (2013.01)

(58) Field of Classification Search
None
See application file for complete search history.

(56) References Cited

U.S. PATENT DOCUMENTS

| | | | |
|---|---|---|---|
| 5,004,863 A | 4/1991 | Umbeck | |
| 5,159,135 A | 10/1992 | Umbeck | |
| 5,792,933 A | 8/1998 | Ma | |
| 6,096,950 A | 8/2000 | John | |
| 6,166,294 A | 12/2000 | Kasukabe et al. | |
| 6,259,003 B1 | 7/2001 | Fujisawa et al. | |
| 7,314,974 B2 * | 1/2008 | Cao ..................... | C07K 14/195 800/288 |
| 2003/0106097 A1 | 6/2003 | Haigler et al. | |
| 2003/0134120 A1 | 7/2003 | Kim et al. | |
| 2013/0081154 A1 | 3/2013 | Meulewaeter et al. | |

FOREIGN PATENT DOCUMENTS

| | | | |
|---|---|---|---|
| EP | 1339859 B1 | 9/2003 | |
| WO | 9215675 A1 | 9/1992 | |
| WO | 9606932 A1 | 3/1996 | |
| WO | 9830698 A1 | 7/1998 | |
| WO | 0071733 A1 | 11/2000 | |
| WO | 0210377 A1 | 2/2002 | |
| WO | 0210413 A1 | 2/2002 | |
| WO | 2006136351 A2 | 12/2006 | |
| WO | 2007039314 A2 | 4/2007 | |
| WO | WO-2008034648 A1 * | 3/2008 | ......... C12N 15/8218 |
| WO | 2008083969 A2 | 7/2008 | |
| WO | 2011089021 A1 | 7/2011 | |
| WO | WO-2011089021 A1 * | 7/2011 | ........... C12N 9/1051 |
| WO | 2012048807 A1 | 4/2012 | |
| WO | 2012093032 A1 | 7/2012 | |

OTHER PUBLICATIONS

An, Yong-Qiang, et al., Strong, constitutive expression of the *Arabidopsis* ACT2/ACT8 actin subclass in vegetative tissues, The Plant Journal, 1996, pp. 107-121, vol. 10. 1.
Buchholz, Wallace G., et al., Cyclophilins are encoded by a small gene family in rice, Plant Molecular Biology, 1994, pp. 837-843, vol. 25.
Cristensen, Alan H., et al., Maize polyubiquitin genes: structure, thermal perturbation of expression and transcript splicing, and promoter activity following transfer to protoplasts by electroporation, Plant Molecular Biology, 1992, pp. 675-689, vol. 18.
Crossway, Anne, et al., Integration of foreign DNA following microinjection of tobacco mesophyll protoplasts, Mol. Gen. Genet, 1986, pp. 179-185, vol. 202.
Depater, B. Sylvia, et al., The promoter of the rice gene GOS2 is active in various different monocot tissues and binds rice nuclear factor ASF-1, The Plant Journal, 1992, pp. 837-844, vol. 2, 6.
Desai, Priti N., et al., Production of heterologous proteins in plants: Strategies for optimal expression, Biotechnology Advances, 2010, pp. 427-435, vol. 28.
Klein, T.M., et al., High-velocity microprojectiles for delivering nucleic acids into living cells, Nature, May 1987, pp. 70-73, vol. 327.
Krens, F.A., et al., In vitro transformation of plant protoplasts with Ti-plasmid DNA, Nature, Mar. 1982, pp. 72-74, vol. 296.
Lagorce, Arnaud, et al., Involvement of GFA1, which encodes glutamine-fructose-6-phosphate amidotransferase, in the activation of the chitin synthesis pathway in response to cell-wall defects in *Saccharomyces cerevisiae*, Eur. J. Biochem, 2002, pp. 1697-1707, vol. 269.

(Continued)

*Primary Examiner* — Brent T Page

(57) ABSTRACT

An isolated nucleic acid molecule is provided comprising a nucleotide sequence which encodes a glutamine:fructose-6-phosphate amidotransferase from *E. coli* which is particularly suitable for expression in cotton plant cells. The invention also relates to plant cells or plants, in particular to cotton plant cells or cotton plants which produce an increased amount of positively charged polysaccharides in their cell walls. Furthermore methods and means are provided to increase the content of positively charged polysaccharides in the cell walls of cotton cells, in particular in cotton fibers. Fibers obtained from such cotton plants have an altered chemical reactivity which can be used to attach reactive dyes or other textile finish reagents to these fibers.

7 Claims, 2 Drawing Sheets
Specification includes a Sequence Listing.

(56) References Cited

OTHER PUBLICATIONS

Lepetit, Marc, et al., A plant histone gene promoter can direct both replication-dependent and -independent gene expression in transgenic plants, Mol. Gen. Genet, 1992, pp. 276-285, vol. 231.

Lui, X.D., et al., Chitosan coated cotton fiber: preparation and physical properties, Carbohydrate Polymers, 2001, pp. 233-238, vol. 44.

Mayer, F.C., et al., Pathway of Uridine Diphosphate N-Acetyl-D-Glucosamine Biosynthesis in Phaseolus aureus1, Plant Physiol., 1968, pp. 1097-1107, vol. 43.

McElroy, David, et al., Isolation of an efficient actin promoter for use in rice transformation, The Plant Cell, Feb. 1990, pp. 163-171, vol. 2.

Negrutiu, I., et al., Hybrid genes in the analysis of transformation conditions, Plant Molecular Biology, 1987, pp. 363-373, vol. 8.

Nilsson, Ove, et al., The Agrobacterium rhizogenes rolB and rolC promoters are expressed in pericycle cells competent to serve as root initials in transgenic hybrid aspen, Physiologia Plantarium, 1997, pp. 456-462, vol. 100.

Odell, T., et al., Identification of DNA sequences required for activity of the cauliflower mosaic virus 35S promoter, Nature, Feb. 1985, pp. 810-812, vol. 313.

Ruan, Yong-Ling, et al., A Fiberless Seed mutation in Cotton is associated with lack of fiber cell initiation in ovule epidermis and alterations in sucrose synthase expression and carbon partitioning in developing seeds1, Plant Physiol, 1998, pp. 399-406, vol. 118.

Ruan, Yong-Ling, et al., Pathway and control of sucrose import into initiating cotton fibre cells, Aust. J. Plant Physiol, 2000, pp. 795-800, vol. 27.

Shillito, R.D., et al., High efficiency direct gene transfer to plants, Bio. Technol., 1985, pp. 1099-1102, vol. 3.

Wang, Liangjiang, et al., Comparative analysis of expressed sequences reveals a conserved pattern of optimal codon usage in plants, Plant Mol. Biol., 2006, pp. 699-710, vol. 61.

Written Opinion of the International Searching Authority for PCT/EP2015/055603, dated Sep. 24, 2015.

\* cited by examiner

Figure 1

```
   1  atgtgcggaa ttgttggcgc aatagcacaa agggacgtag cagaaatcct
  51  tcttgaagga ctccgtcgtc tggaatacag aggatatgat tctgccggtc
 101  tagccgttgt agatgccgaa ggtcacatga cacgtctaag acgtctgggt
 151  aaggttcaaa tgctggctca agcagccgaa gaacatcctt tacatggtgg
 201  cacaggtatt gctcacacta gatgggctac tcacggtgaa ccttcagagg
 251  taaatgctca tccacatgtc tctgagcaca ttgtggtcgt tcacaacggg
 301  atcatcgaaa accatgaacc acttcgagaa gagctgaaag ctcgtggcta
 351  tactttcgtt tcagagacag acactgaggt gattgctcat ctcgtgaact
 401  gggaactgaa acaaggggga actctgagag aggctgttct acgtgctatc
 451  cctcaattac gtggtgctta cgggacagtg atcatggatt caagacaccc
 501  agatacactg ctggcagcaa ggtctggtag tccactggtg attggactgg
 551  ggatgggaga aaactttatc gcttcggatc aactggctct gttacctgtg
 601  acacggagat ttatcttcct tgaagagggc gatatcgcgg aaataactcg
 651  acgtagcgta aacatcttcg ataaaaccgg agcagaagta aaacgccagg
 701  atatcgaatc caatcttcaa tacgacgccg gcgataaagg catataccga
 751  cactacatgc agaaagagat ctacgagcaa ccgaacgcta tcaagaatac
 801  ccttactggg cgtatctcac atggtcaggt tgacttatct gaactgggac
 851  caaacgcaga cgaactactg tcgaaggtag aacatattca gatcctcgcg
 901  tgtggtactt cttataactc tggtatggtc agtcgctatt ggtttgaatc
 951  actggcagga attccttgcg acgtcgaaat tgcctcggaa ttcagatatc
1001  gcaagtctgc agtaagacgc aacagcctga tgataacgtt atctcagtct
1051  ggagaaacgg ctgatacact ggctggatta cgtctgtcaa aagagcttgg
1101  ctaccttggt tctctagcaa tctgtaacgt tcctggtagc tctcttgtgc
1151  gagaatctga tcttgctctt atgactaacg ctggtacaga aatcggggtg
1201  gcatccacaa aagcatttac aactcaactt acggtgctgc taatgcttgt
1251  ggcaaagctg tctagactca aaggtctaga tgcctccatc gagcatgata
1301  tcgttcatgg tctgcaagct cttcctagcc gaattgagca gatgctgtca
1351  caagacaaaa ggattgaagc cctggcagaa gatttctcag acaagcatca
1401  cgctttgttt ctcggtcgtg gcgatcagta cctatcgct ctcgaaggcg
1451  cattgaagct caaagagatc tcctatatac acgctgaagc ttacgctgca
1501  ggcgaactga acacggacc tctagctctt attgacgcag atatgcccgt
1551  tatcgtcgtt gcaccaaaca acgaattgct ggagaagctg aaatcaaata
1601  ttgaagaggt acgtgcaaga ggcggacaac tttatgtctt cgctgagcaa
1651  gatgccggtt ttgtaagtag cgataacatg cacatcatcg agatgcctca
1701  cgtggaagag gtgattgctc cgatcttcta cacagttccc ctgcagcttc
1751  tggcttatca cgttgcccctt atcaaaggaa ctgacgttga ccagccaagg
1801  aatctcgcaa agtcagtaac ggttgagtaa
```

Figure 2

MCGIVGAIAQRDVAEILLEGLRRLEYRGYDSAGLAVVDAEGHMTRLRRLGKVQMLAQAEEHPLHGGTGIA
HTRWATHGEPSEVNAHPHVSEHIVVVHNGIIENHEPLREELKARGYTFVSETDTEVIAHLVNWELKQGGT
LREAVLRAIPQLRGAYGTVIMDSRHPDTLLAARSGSPLVIGLGMGENFIASDQLALLPVTRRFIFLEEGD
IAEITRRSVNIFDKTGAEVKRQDIESNLQYDAGDKGIYRHYMQKEIYEQPNAIKNTLTGRISHGQVDLSE
LGPNADELLSKVEHIQILACGTSYNSGMVSRYWFESLAGIPCDVEIASEFRYRKSAVRRNSLMITLSQSG
ETADTLAGLRLSKELGYLGSLAICNVPGSSLVRESDLALMTNAGTEIGVASTKAFTTQLTVLLMLVAKLS
RLKGLDASIEHDIVHGLQALPSRIEQMLSQDKRIEALAEDFSDKHHALFLGRGDQYPIALEGALKLKEIS
YIHAEAYAAGELKHGPLALIDADMPVIVVAPNNELLEKLKSNIEEVRARGGQLYVFAEQDAGFVSSDNMH
IIEMPHVEEVIAPIFYTVPLQLLAYHVALIKGTDVDQPRNLAKSVTVE

COTTON FIBERS WITH INCREASED GLUCOSAMINE CONTENT

CROSS REFERENCE TO RELATED APPLICATIONS

This application is a national stage application under 35 U.S.C. § of PCT Application No. PCT/EP15/055603, filed Mar. 18, 2015, which claims the benefit of European Patent Application Serial No. 14161153.3 filed Mar. 21, 2014, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "BCS 14-2002-WO1_ST25.txt," created on Mar. 21, 2014, and having a size of 42 kilobytes and is filed concurrently with the specification. The sequence listing contained in this ASCII formatted document is part of the specification and is herein incorporated by reference in its entirety.

FIELD OF THE INVENTION

The present invention relates to the modification of the chemical reactivity of cotton fibers. In particular, the present invention provides cotton fibers comprising positively charged oligosaccharides such as oligo-N-acetylglucosamines or oligo-glucosamines. Due to the amino groups these fibers have a modified reactivity which can be exploited for attaching other substances to the fibers to alter their characteristics. Such substances can e.g. be reactive dyes or other reactants such as flame retardants, water, oil and soil repellents, anticrease agents, softeners, antistatic agents, fluorescent whitening agents etc.

The current invention provides methods and means to increase the efficiency of production of glucosamine oligomers in cotton plant cells such as fiber cells.

BACKGROUND OF THE INVENTION

Cotton fiber is the single most important textile worldwide. About 80 million acres of cotton are harvested annually across the globe. Cotton is the fifth largest crop in the U.S. in terms of acreage production, with an average of 10.3 million acres planted in the years 2006 to 2008. About 90% of cotton grown worldwide is *Gossypium hirsutum* L., whereas *Gossypium barbadense* accounts for about 8%.

However, like other natural cellulose containing fibers, cotton fibers do not possess the chemical versatility of synthetic fibers, due to the relative inert nature of the β-1-4 linked glucose monomers in cellulose. This relative inert nature is e.g. apparent during the dyeing process of cotton fibers and fabrics.

Generally two types of dyes are used to color cotton: direct dyes and fiber-reactive dyes, which are both anionic molecules. Cotton itself develops an anionic charge in water, so that without special treatment, the uptake of dye by the fiber or fabric is quite elaborate. Direct dyes create a relatively weak hydrogen bond with the cellulose polymer forming a semi-permanent attachment. Direct dyes are easier to use and less expensive than fiber-reactive dyes, but do not withstand well washing. Fiber-reactive dyes are molecules that combine chromophores with a reactive group that forms strong covalent bonds with the fiber via reaction with hydroxyl groups. The covalent bonds provide a good resistance of the dyed fiber against laundering. Colorfastness can be improved using cationic fixatives.

During the dyeing process using reactive dyes, large amounts of electrolytes are needed to shield the anionic dyes from the anionic fiber charges. Unreacted dyes (up to 40%) need to be removed by a washing step, generating large volumes of wastewater, also containing the above mentioned electrolytes.

Providing the cellulose fiber with a positive electric charge, e.g. by incorporation of positively charged chemical compounds such as positively charged polysaccharides, could therefore improve the dyeability of natural cellulose fibers, as well as improve any chemical reaction of the modified cellulose fiber with negatively charged chemical compounds. It would also make the use of acidic dyes possible.

Several publications have described the incorporation into or coating of chitosan oligomers into cellulose fibers to make chitosan/cellulose blends, yarns or fabrics. Chitosan is a positively charged polymer of glucosamine, which can be obtained by deacetylation of chitin, e.g. by alkalic treatments. Chitin itself is a polymer of βe1-4 linked N-acetylglucosamine (GlcNAc). Based on the physiological function of chitosan in inhibiting e.g. dermatophytes, many functional clothes, fabrics and fibers employ cellulose-chitosan blend fibers, cellulose fiber-chitosan conjugates and fabrics coated with chitosan-containing resins.

US patent application US2003/0134120 describes the coating of natural fibers with chitosan.

Liu et al. (Carbohydrate Polymers 44(2003) 233-238) describe a method for coating cotton fibers with chitosan, by oxidation of the cotton thread with potassium periodate at 60° C. in water and subsequent treatment with a solution of chitosan in aqueous acetic acid. With the chitosan coating, the cotton fiber surface became physiologically and biologically active. Since the chemical reactivity of the amino group is greater than the hydroxyl group of cellulose monomers, the fiber has more potential for further chemical modification. Moreover, the smooth surface of the cotton fiber became coarse, suggesting a greater potential for drug absorption and controlled release thereof.

WO2006/136351 provides methods and means for the modification of the reactivity of plant cell walls, particularly as they can be found in natural fibers of fiber producing plants by inclusion of positively charged oligosaccharides or polysaccharides into the cell wall. This can be conveniently achieved by expressing a chimeric gene encoding an N-acetylglucosamine transferase, particularly an N-acetylglucosamine transferase capable of being targeted to the membranes of the Golgi apparatus in cells of a plant. One of the applications is increased dyeability.

WO2011/089021 provides methods and means for the modification of the reactivity of plant secondary cell walls, particularly in cotton cell walls found in cotton fibers. This can be conveniently achieved by expressing a chimeric gene encoding a *Saprolegnia monoica* chitin synthase in cotton plants.

WO2012/048807 provides alternative methods and means to produce positively charged oligosaccharides in the plant cell wall by introducing into said plant cell a Nodulation C (NOD C) protein fused to a heterologous Golgi signal anchor sequence.

The polysaccharide chitin is built from N-acetylglucosamine residues. It is synthesized from UDP-N-acetylglucosamine which is the end-product of the hexosamine biosynthesis pathway also active in plants (Mayer et al. 1968, Plant Physiol. 43, 1097-1107). The first and rate limiting step of this pathway is the conversion of glutamine to glucosamine-6-phosphate which is catalyzed by the enzyme glutamine:fructose-6-phosphate-amidotransferase (GFAT).

WO 2007/039314 describes transgenic plants having the activity of a hyaluronan synthase and additionally an increased glutamine:fructose-6-phosphate amidotransferase (GFAT) activity. These plants synthesize an increased amount of hyaluronan compared to plants having only the activity of a hyaluronan synthase. Like chitin, hyaluronan is synthesized from UDP-N-acetylglucosamine.

WO 2011/089021 discloses transgenic cotton plants comprising a chimeric chitin synthase gene and a chimeric glutamine:fructose-6-phosphate-amidotransferase gene under the control of a cotton selective promotor. Fibers from these transgenic cotton plants have an increased amount of N-acetylglucosamine polymers which are evenly distributed throughout the cell wall.

Yet there remains a need for improved methods and means to produce cotton fibers which comprise an increased level of positively charged polysaccharides such as oligo-N-acetylglucosamines or oligo-glucosamines. These and other problems are solved as described hereinafter in the summary, detailed embodiments, examples, drawings and claims.

SUMMARY OF THE INVENTION

The invention shows that the expression of a chimeric gene comprising
(a) a nucleotide sequence according to SEQ ID 1, or
(b) a variant thereof which differs from SEQ ID 1 in one or more nucleotides provided that in total it differs from SEQ ID 1 in no more than 20 nucleotides,
which encodes a glutamine:fructose-6-phosphate-amidotransferase (GFAT) polypeptide according to SEQ ID 2, in plant cells such as cotton plant cells unexpectedly leads to an increase in the glucosamine content of the cells.

In a second embodiment the invention provides a chimeric gene comprising the following operably linked DNA regions:
(a) a plant-expressible promotor such as a fiber-preferential promotor,
(b) a DNA region coding for a GFAT polypeptide wherein said GFAT is encoded by a nucleotide sequence according to SEQ ID 1 or said variant thereof and
(c) optionally a DNA region involved in transcription termination and polyadenylation.

In another embodiment the invention provides a cotton plant cell comprising a chimeric gene comprising the following operably linked DNA regions:
(a) a plant-expressible promotor such as a fiber-preferential promotor,
(b) a DNA region coding for a GFAT polypeptide wherein said GFAT is encoded by a nucleotide sequence according to SEQ ID 1 or said variant thereof and
(c) optionally a DNA region involved in transcription termination and polyadenylation.

In some embodiments the invention provides a plant cell which in addition to said first chimeric gene comprises a second chimeric gene comprising the following operably linked DNA regions:
(a) a plant-expressible promotor such as a fiber-preferential promotor,
(b) a DNA sequence coding for a chitin synthase polypeptide and
(c) optionally a DNA region involved in transcription termination and polyadenylation.

In yet another embodiment the invention provides a cotton plant consisting of the plant cells as herein described.

The invention also provides fibers such as cotton fibers which can be obtained from the plant as herein described. Furthermore a yarn or a fabric made from the fibers is provided.

In another embodiment of the invention a method is provided to produce cotton fibers with positively charged polysaccharides, such as oligo-N-acetylglucosamines or oligo-glucosamines comprising the steps of
i) expressing a chimeric gene comprising a GFAT encoding nucleotide sequence according to the invention in a cotton plant cell,
ii) regenerating a cotton plant from cotton plant cells of step i) and
iii) optionally isolating fibers from said cotton plant.

In yet another embodiment of the invention, said method to produce cotton fibers with positively charged polysaccharides comprises the steps of
i) expressing a first chimeric gene comprising a GFAT-encoding nucleotide sequence as described herein before and a second chimeric gene comprising a nucleotide sequence which encodes a chitin synthase,
ii) regenerating a cotton plant from cotton plant cells of step i) and
iii) optionally isolating fibers from said cotton plant.

The invention further relates to the use of a nucleic acid molecule as herein described to produce a cotton plant with positively charged polysaccharides in the fibers.

The invention also relates to the use of a nucleic acid molecule as herein described to increase the amount of positively charged polysaccharides in cotton fibers.

DESCRIPTION OF FIGURES

FIG. 1: Nucleotide sequence of the synthetic nucleic acid molecule which encodes the glutamine:fructose-6-phosphate amidotransferase (GFAT) of *E. coli* according to SEQ ID 2 (SEQ ID 1).

FIG. 2: Amino acid sequence of the glutamine:fructose-6-phosphate amidotransferase (SEQ ID 2) of *E. coli*.

DETAILED DESCRIPTION OF THE INVENTION

The current invention is based upon the unexpected finding that expression of a nucleotide sequence according to SEQ ID 1 which encodes a glutamine:fructose-6-phosphate-amidotransferase (GFAT) in plant cells, particularly in cotton plant cells of cotton plants leads to the production of an increased amount of positively charged polysaccharides such as oligo-N-acetylglucosamines or oligo-glucosamines in plant cells or fibers of such plants such as cotton fibers, compared to plant cells or fibers not comprising a GFAT protein or compared to plant cells expressing a GFAT encoding gene known in the art which is not optimized for expression in cotton plant cells.

This unexpected finding can also be achieved by expression of a variant of SEQ ID 1 in a plant cell, particularly in a cotton plant cell, which encodes a glutamine:fructose-6-phosphate-amidotransferase according to SEQ ID 2, wherein said variant differs from SEQ ID 1 in one or more nucleotides provided that in total it differs in no more than 20 nucleotides from SEQ ID 1.

Thus, in a first embodiment, the invention provides an isolated nucleic acid molecule comprising
  i) a nucleotide sequence according to SEQ ID 1,
  ii) or a variant thereof, wherein one or more nucleotides differ from the nucleotide sequence of SEQ ID 1, provided that said variant differs in no more than 20 nucleotides from SEQ ID 1,
which encodes a glutamine:fructose-6-phosphate-amidotransferase (GFAT) according to SEQ ID 2
  iii) or a complementary sequence of i) or ii).

SEQ ID 1 encodes a glutamine:fructose-6-phosphate-amidotransferase from *E. coli*. The corresponding amino acid sequence of the protein is described in SEQ ID 2. This enzyme catalyzes the conversion of fructose-6-phosphate and glutamine into glucosamine-6-phosphate and glutamate as a side product. It has been described in WO2007/039314 for the production of hyaluronan in plants. During the hexosamine pathway, glucosamine-6-phosphate is further converted to UDP-N-acetylglucosamine which in turn serves as starting material for the synthesis of glycosaminoglycans such as hyaluronan or chitin if the appropriate enzymes are present.

WO2007/039314 discloses a GFAT nucleotide sequence which was derived from the *E. coli* gene coding for GFAT but was adapted to the use of codons in plant cells. The nucleotide sequence disclosed as SEQ ID 1 in the current application varies from the nucleotide sequence described in WO2007/039314 by about 25%. While the sequence disclosed in WO2007/039314 was optimized for expression in plant cells in general, the expression of a chimeric gene comprising a nucleotide sequence according to SEQ ID 1 leads to particularly good results in cotton cells. Cotton cells comprising a plant-expressible nucleotide sequence according to SEQ ID 1 or a variant thereof which encodes a GFAT protein from *E. coli* according to SEQ ID 2 and which differs from SEQ ID 1 in one or more nucleotides provided that in total it does not differ in more than 20 nucleotides from SEQ ID 1, or cotton plants made up by such cotton plant cells, produce an increased amount of glucosamine compared to cotton cells expressing a nucleotide sequence as disclosed in WO2007/039314 or plants made up by such cotton cells (see experimental data).

As used herein "no more than 20 nucleotides difference from SEQ ID 1", means e.g. 20 nt, 19 nt, 18 nt, 17 nt, 16 nt, 15 nt, 14 nt, 13 nt, 12 nt, 11 nt, 10 nt, 9 nt, 8 nt, 7 nt, 6 nt, 5 nt, 4 nt, 3 nt, 2 nt or 1 nt different from SEQ ID 1, while still encoding the glutamine:fructose-6-phosphate-amidotransferase (GFAT) according to SEQ ID 2.

Nucleic acids can be DNA or RNA, single- or double-stranded. Nucleic acids can be synthesized chemically or produced by biological expression in vitro or even in vivo. Nucleic acids can be chemically synthesized using appropriately protected ribonucleoside phosphoramidites and a conventional DNA/RNA synthesizer. In connection with the chimeric gene of the present disclosure, DNA includes cDNA and genomic DNA.

In another embodiment of the invention, a chimeric gene is provided comprising as operably linked DNA regions
  (a) a plant-expressible promotor such as a fiber-preferential promotor,
  (b) a DNA region coding for a GFAT polypeptide wherein said GFAT is encoded by a nucleotide sequence as described herein above and
  (c) optionally a DNA region involved in transcription termination and polyadenylation.

As used herein, the term "plant-expressible promoter" means a DNA sequence which is capable of controlling (initiating) transcription in a plant cell. This includes any promoter of plant origin, but also any promoter of non-plant origin which is capable of directing transcription in a plant cell, i.e. certain promoters of viral or bacterial origin such as the CaMV35S, the subterranean clover virus promoter No 4 or No 7 (WO9606932) or T-DNA gene promoters and the like.

In one embodiment of the invention, the promoter may be a heterologous promoter not naturally associated with the DNA region operably linked to it.

It will be clear that constitutive plant-expressible promoters may be suitable for the invention. Examples of constitutive promoters include the promoter from the actin gene (McElroy et al. (1990) Plant Cell 2: 163-171), the CaMV35S promoter (Odell et al. (1985) Nature 313: 810-812), the CaMV19S promoter (Nilsson et al. (1997) Physiol. Plant. 100: 456-462), the GOS2 promoter (de Pater et al. (1992) Plant. J. 2(6): 837-44), the promoter from ubiquitin gene (Christensen et al. (1992) Plant Mol. Biol. 18: 675-689), the promoter from rice cyclophilin gene (Buchholz et al. (1994) Plant. Mol. Biol. 25(5): 837-43), the promoter from the maize H3 histone gene (Lepetit et al. (1992) Mol. Gen. Genet. 231: 276-285) or the promoter from the actin 2 gene (An et al. (1996) Plant J. 10(1): 107-121).

It is also clear that inducible promoters, such as a temperature inducible or a chemically inducible promoter or a promoter which is responsive to developmental cues, may be used in accordance with the invention. Tissue selective promoters may also be used.

In a preferred embodiment of the invention, the chimeric gene comprises a fiber-preferential or fiber-selective promoter. The term "fiber-preferential" or "fiber-selective", with respect to the expression of a gene or with respect to a promoter, refers to, for practical purposes, the highly specific expression of a gene or expression directed by a promoter, in fiber cells of plants, such as cotton plants. In other words, transcript levels of a DNA in tissues different of fiber cells is either below the detection limit or very low (less than about 0.2 picogram per microgram total RNA).

The term "fiber-preferential" or "fiber-cell preferential" with respect to the expression of a DNA in accordance with this invention, refers to an expression pattern whereby the DNA is expressed predominantly in fiber cells or fibers, but expression can be identified in other tissues of the plant. Preferably, the expression in fiber cells is about 2 to about 10 times higher in the fiber cells than in other tissues.

Such promoters (all herein incorporated by reference) include the promoter from cotton from a fiber-specific ❑uch prom❑❑ e (as described in WO0210377), the promoter from cotton from a fiber-specific actin gene (as described in WO0210413), the promoter from a fiber-specific lipid transfer protein gene from cotton (as described in U.S. Pat. No. 5,792,933), a promoter from an expansion gene from cotton (WO9830698) or a promoter from a chitinase gene in cotton (US2003106097) or the promoters of the fiber-specific genes described in U.S. Pat. No. 6,259,003 or U.S. Pat. No. 6,166,294 or the promotors derived from the E6 family as disclosed in U.S. Pat. No. 6,096,950. Fiber selective promoters as described in WO08/083969 (from cotton glucanase genes), WO12/093032 (from cotton FS18 or SCW-PRP gene) or US 2013/0081154 (from cotton FB8-like genes) are also suitable plant-expressible promoters. Also suitable for the invention is the promoter disclosed in EP13172094 comprising the nucleotide sequence of SEQ ID No. 5 as described therein from nucleotide position 4208 to nucleotide position 5615 or having the nucleotide sequence of SEQ ID No. 5 from nucleotide position 75 to 1482.

The chimeric genes as herein described optionally comprise a DNA region involved in transcription termination and polyadenylation. A variety of DNA regions involved in transcription termination and polyadenylation functional in plants are known in the art and those skilled in the art will be aware of terminator and polyadenylation sequences that may be suitable in performing the methods herein described. The polyadenylation region may be derived from a natural gene, from a variety of other plant genes, from T-DNA genes or even from plant viral genomes. The 3' end sequence to be added may be derived from, for example, the nopaline synthase or octopine synthase genes, or alternatively from another plant gene, or from any other eukaryotic gene.

In a particular embodiment of the invention a cotton plant cell is provided comprising a chimeric gene comprising as operably linked DNA regions
  (a) a plant-expressible promotor such as a fiber-preferential promotor,
  (b) a DNA region coding for a GFAT polypeptide wherein said GFAT is encoded by a nucleotide sequence as herein described and
  (c) optionally a DNA region involved in transcription termination and polyadenylation.

The chimeric gene may be introduced into a plant cell by methods well-known in the art. "Introducing" in connection with the present application relates to the placing of genetic information in a plant cell or plant by artificial means. This can be effected by any method known in the art for introducing RNA or DNA into plant cells, tissues, protoplasts or whole plants.

The term "introducing" may refer to introduction of an exogenous DNA molecule to a plant cell by transformation, optionally followed by regeneration of a plant from the transformed plant cell. The term may also refer to introduction of the recombinant DNA molecule by crossing of a transgenic plant comprising the recombinant DNA molecule with another plant and selecting progeny plants which have inherited the recombinant DNA molecule or transgene. Yet another alternative meaning of providing refers to introduction of the recombinant DNA molecule by techniques such as protoplast fusion, optionally followed by regeneration of a plant from the fused protoplasts.

It will be clear that the methods of transformation used are of minor relevance to the current invention. Transformation of plants is now a routine technique. Advantageously, any of several transformation methods may be used to introduce the nucleic acid/gene of interest into a suitable ancestor cell. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens et al. (1982) Nature 296: 72-74; Negrutiu et al. (1987) Plant. Mol. Biol. 8: 363-373); electroporation of protoplasts (Shillito et al. (1985) Bio/Technol. 3: 1099-1102); microinjection into plant material (Crossway et al. (1986) Mol. Gen. Genet. 202: 179-185); DNA or RNA-coated particle bombardment (Klein et al. (1987) Nature 327: 70) infection with (nonintegrative) viruses and the like.

Methods to transform cotton plants are also well known in the art. Agrobacterium-mediated transformation of cotton has been described e.g. in U.S. Pat. No. 5,004,863 or in U.S. Pat. No. 6,483,013 and cotton transformation by particle bombardment is reported e.g. in WO 92/15675. Other suitable cotton transformation methods are disclosed e.g. in WO 00071733 and U.S. Pat. No. 5,159,135, which disclosures are incorporated by reference herein as if fully set forth.

The recombinant DNA molecules according to the invention may be introduced into plants in a stable manner or in a transient manner using methods well known in the art. The chimeric genes may be introduced into plants, or may be generated inside the plant cell as described e.g. in EP 1339859.

In yet another embodiment, the invention provides a cotton plant cell as described herein above wherein said cotton plant cell additionally comprises a second chimeric gene comprising the following operably linked DNA regions:
  (a) a plant-expressible promotor such as a fiber-preferential promotor,
  (b) a DNA sequence coding for a chitin synthase polypeptide and
  (c) optionally a DNA region involved in transcription termination and polyadenylation.

Several embodiments and specifications on what is meant by the term "plant-expressible promotor" are given above and equally apply for the second chimeric gene comprising a DNA region encoding a chitin synthase. The same is true for the specifications given above on the DNA region involved in transcription termination and polyadenylation and also for methods and means to provide a plant cell with a chimeric gene.

The first chimeric gene and the second chimeric gene can be introduced into a plant cell individually in any order or simultaneously. They can be introduced on the same vector or on separate vectors.

The chitin synthase can be any protein having the enzymatic activity of a chitin synthase (EC 2.4.1.16), i. e. that converts UDP-N-acetyl-D-glucosamine into chitin and UDP. A chitin synthase catalyzes the reaction: UDP-N-acetyl-alpha-D-glucosamine+(1,4-(N-acetyl-beta-D-glucosaminyl))(n)<=>UDP+(1,4-(N-acetyl-beta-D-glucosaminyl))(n+1). Suitable for the present invention is any chitin synthase derived from any organism. Examples for suitable chitin synthases are chitin synthase from *Saprolegnia monoica* (WO 2011/089021) or chitin synthases of the NOD C type as described in WO 2006/136351 or in WO 2012/048807 for example.

In a particular embodiment of the invention, the chitin synthase in said cotton plant cell as described before is an N-acetylglucosamine transferase of the NOD C type. Particular good results are achieved if said chitin synthase polypeptide comprises a Golgi localization signal.

Although good results have been achieved with plant cells comprising a chitin synthase activity in addition to the GFAT activity, the GFAT activity as obtained by means described in the invention can also beneficially be combined with any enzymatic activity that leads to the production of glycosaminoglycans from the GFAT product glucosamine-6-phosphate or from UDP-N-acetylglucosamine. As described in the introduction, glucosamine-6-phosphate is further converted to UDP-N-acetylglucosamine via the hexosamine pathway in plants. One such enzymatic activity that converts UDP-N-acetylglucosamine into glycosaminoglycans other than chitin is that of a hyaluronan synthase. Thus a hyaluronan synthase can also be used instead of a chitin synthase.

In another particular embodiment the invention provides a plant consisting essentially of plant cells comprising a chimeric gene herein described before. The chimeric gene can be a first chimeric gene comprising a GFAT encoding region or a first and a second chimeric gene as described before. In a particular embodiment the plant is a cotton plant.

"Cotton" or "cotton plant" as used herein can be any variety useful for growing cotton. The most commonly used cotton varieties are *Gossypium barbadense, G. hirsutum, G. arboreum* and *G. herbaceum*. Further varieties include *G. africanum* and *G. raimondii*. Also included are progeny from crosses of any of the above species with other species or crosses between such species.

A cotton plant cell may be any cell comprising essentially the genetic information necessary to define a cotton plant, which may, apart from the chimeric gene disclosed herein, be supplemented by one or more further transgenes. Cells may be derived from the various organs and/or tissues forming a cotton plant, including but not limited to fruits, seeds, embryos, reproductive tissue, meristematic regions, callus tissue, leaves, roots, shoots, flowers, vascular tissue, gametophytes, sporophytes, pollen, and microspores.

Whereas certain plant cells according to the invention may be able to regenerate into complete plants, in some embodiments said plant cells cannot further develop or regenerate into a complete plant. In one embodiment of the invention, fiber cells are committed. Mature fiber cells are dead cells.

The invention is also directed towards fiber-producing plants comprising one or more recombinant construct according to the invention. Although the nucleotide sequence encoding the GFAT protein has been optimized for expression in cotton plants, it is thought that the coding region could also be beneficially used in other fiber producing plants such as hemp, jute, flax and woody plants including but not limited to *Pinus* spp., *Populus* spp., *Picea* spp., *Eucalyptus* spp. etc. The plant cell may be derived from any trichome-producing plant.

The plants according to the invention can be used in a conventional breeding scheme to produce more plants with the same characteristics or to introduce the chimeric gene according to the invention in other varieties of the same or related plant species, or in hybrid plants. Seeds obtained from the transformed plants contain the chimeric genes of the invention as a stable genomic insert and are also encompassed by the invention.

The term "plant" as used herein encompasses whole plants, ancestors and progeny of the plants and plant parts, including seeds, shoots, stems, leaves, roots (including tubers), flowers, fibers and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

In a specific embodiment the invention provides cotton fibers obtainable from a cotton plant according to the invention.

The cotton fibers according to the invention can be distinguished from naturally occurring cotton fibers, i. e. cotton fibers obtained from an isogenic line which does not comprise a nucleic acid sequence according to the invention, by the increased content of positively charged polysaccharides such as oligo-N-acetylglucosamines or oligo-glucosamines. The GlcNAc polymers or oligo-glucosamines can be detected directly. Alternatively, positively charged polysaccharides in the cotton fibers can be detected by measuring the glucosamine content after treatment with trifluoro-acetic acid (TFA) to hydrolyze the polysaccharides. The cotton fibers according to the invention may also be distinguished by their increased nitrogen content. Due to the reactivity of the nitrogen-containing groups within the glucosamine-polymers, cotton fibers according to the invention are characterized by an altered chemical reactivity compared to fibers obtained from cotton plants which do not comprise a nucleic acid region encoding a GFAT polypeptide as herein described. Fibers according to the invention have an increased capacity to react with dyes or other suitable chemicals via the nitrogen-containing groups.

Cotton fibers according to the invention are characterized by an increased content of positively charged polysaccharides such as oligo-N-acetylglucosamines or oligo-glucosamines. "Increased content" means that the amount of positively charged polysaccharides present in the plant cells or fibers is higher than in plant cells or fibers not comprising a GFAT protein or compared to plant cells or fibers expressing a GFAT encoding gene known in the art which is not optimized for expression in cotton plant cells. In one embodiment, the content of glucosamine (GlcN) is at least twice that of cells or fibers from plants not expressing an artificially introduced gene construct. This background level was observed to be approximately 0.010 to 0.015% GlcN of total fiber weight. Preferably, fibers according to the invention contain more than 0.03% GlcN of total fiber weight. More preferably the GlcN content of fibers according to the invention is more than 0.06%, even more preferably more than 0.08%, most preferably more than 0.10% GlcN of total fiber weight. In another embodiment, the GlcN content of plant cells or cotton fibers according to the invention is at least four times that of cells or fibers from plants not expressing an artificially introduced gene construct. In particularly suitable embodiments of the invention, plant cells or fibers have a GlcN content which is at least five times, preferably at least seven times and most preferably ten times that of cells or fibers from plants not expressing an artificially introduced gene construct.

A "fiber" is botanically defined as a long narrow tapering cell, dead and hollow at maturity with a rigid thick cell wall composed mostly of cellulose and usually lignin. Soft or bast fibers are found in the phloem (inner bark) of dicotyledonous stems (flax, jute, hemp, ramie). Hard or leaf fibers are found in monocot leaf vascular bundles (sisal, manilla hemp, pineapple). Surface fibers grown from the surface of seeds (cotton), leaves or fruits (coconut coir).

"Cotton fiber", as used herein, refers to a seed trichome, more specifically a single cell of a fiber-producing plant, such as cotton, that initiates from the epidermis of the outer integument of the ovules, at or just prior to anthesis. The morphological development of cotton fibers has been well documented (Basra and Malik, 1984, Int Rev of Cytology 89: 65-113; Graves and Stewart, 1988, J. Exp. Bot. 39 (1): 59-69; Ramsey and Berlin, 1976, American Journal of Botany 63 (6): 868-876; Ruan and Chourey, 1998, Plant Physiology 118: 399-406; Ruan et al. 2000, Aust. J. Plant Physiol. 27:795-800; Stewart, 1975, Am. J. Bot. 62, 723-730).

Another embodiment of the invention are therefore plant cell walls such as cell walls from cotton cells, comprising an increased level of positively charged polysaccharides such as oligo-N-acetylglucosamines or oligo-glucosamines compared to cell walls from unmodified plant cells or from plant cells not expressing a GFAT encoding nucleotide sequence as herein described.

The invention also relates to yarns made from fibers according to the invention as well as fabrics made from these yarns.

In another embodiment, the invention provides a method to produce cotton fibers with positively charged polysaccharides, such as oligo-N-acetylglucosamines or oligo-glucosamines, comprising the steps of
  i) expressing a chimeric gene comprising a GFAT encoding region as described above in a cotton plant cell,
  ii) regenerating a cotton plant from cotton plant cells of step i) and
  iii) optionally isolating fibers from said cotton plant.

In a particular embodiment, a method is provided to produce cotton fibers with positively charged polysaccharides such as oligo-N-acetylglucosamines or oligo-glucosamines comprising i) expression of a first chimeric gene comprising a GFAT encoding region according to the invention and a second chimeric gene comprising a chitin synthase encoding region in a cotton plant cell, ii) regenerating a cotton plant from said cotton plant cells and iii) optionally isolating fibers from said cotton plant. Said first and second chimeric gene can be introduced into the plant cell simultaneously or separately in any order as described above.

In another embodiment, a method is provided to produce cotton fibers with an increased content of positively charged polysaccharides such as oligo-N-acetylglucosamines or oligo-glucosamines comprising the steps of i) expressing said first chimeric gene or expressing said first and second chimeric gene in a cotton plant cell, ii) regenerating a cotton plant from said cotton plant cells and iii) optionally isolating fibers from said cotton plant. The term "increased content" is to be understood as described above.

Further, a method is provided for producing cotton fibers with altered chemical reactivity of the fibers comprising the steps of i) expressing a chimeric gene comprising a GFAT encoding region according to the invention in a cotton plant cell, ii) regenerating a cotton plant from said cotton plant cells and iii) optionally isolating fibers from said cotton plant.

In yet another embodiment, a method is provided for producing cotton fibers with altered chemical reactivity of the fibers comprising the steps of i) expressing a first chimeric gene comprising a GFAT encoding region as described above and a second chimeric gene comprising a chitin synthase encoding region in a cotton plant, ii) regenerating a cotton plant from said cotton plant cells and iii) optionally isolating fibers from said cotton plant.

The nucleic acid molecule according to the invention can be used to produce a cotton plant with positively charged polysaccharides such as oligo-N-acetylglucosamines or oligo-glucosamines in the fibers. In particular it can be used to increase the amount of positively charged polysaccharides such as oligo-N-acetylglucosamines or oligo-glucosamines in fibers. It can also be used for the production of cotton fibers with altered chemical reactivity. This might allow the convenient, easy and/or efficient further finish of the fibers. Fibers obtained from a cotton plant according to the invention can e. g. be stained with reactive dyes that bind to the fibers via covalent bonds to the amino groups of the glucosamine residues in the polysaccharides. Alternatively, other substances can be attached via chemical reactions to the amino groups of the glucosamine residues. Substances can also be attached to fibers according to the invention via electrostatic or ionic bonding to the N-containing groups of the polysaccharides. The attachment of other substances to cotton fibers can be beneficial to transfer special properties to the fibers. Such finishes can be but are not limited to dying, attachment of flame retardants, water, oil and soil repellents, anticrease agents, softeners, antistatic agents, fluorescent whitening agents or any other textile finish.

As used herein "comprising" is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids may comprise more nucleotides or amino acids than the cited ones, i. e. may be embedded in a larger nucleic acid or protein. A chimeric gene comprising a DNA region which is functionally or structurally defined, may comprise additional DNA regions etc.

The following non-limiting examples describe the generation of cotton fibers with an increased content of positively charged polysaccharides such as oligo-N-acetylglucosamines or oligo-glucosamines.

Unless stated otherwise in the examples, all recombinant techniques are carried out according to standard protocols as described in "Sambrook J and Russell D W (eds.) (2001) Molecular Cloning: A Laboratory Manual, 3rd Edition, Cold Spring Harbor Laboratory Press, New York" and in "Ausubel F A, Brent R, Kingston R E, Moore D D, Seidman J G, Smith J A and Struhl K (eds.) (2006) Current Protocols in Molecular Biology. John Wiley & Sons, New York".

Standard materials and references are described in "Croy RDD (ed.) (1993) Plant Molecular Biology LabFax, BIOS Scientific Publishers Ltd., Oxford and Blackwell Scientific Publications, Oxford" and in "Brown T A, (1998) Molecular Biology LabFax, 2nd Edition, Academic Press, San Diego". Standard materials and methods for polymerase chain reactions (PCR) can be found in "McPherson M J and Møller S G (2000) PCR (The Basics), BIOS Scientific Publishers Ltd., Oxford" and in "PCR Applications Manual, 3rd Edition (2006), Roche Diagnostics GmbH, Mannheim or www.roche-applied-science.com".

Description of Sequences

Reference is made throughout the application to the following sequences represented in the sequence listing named "BCS14-2002_ST25", which is 42 kB (size as measured in Microsoft Windows®), contains 4 sequences SEQ ID NO: 1 through SEQ ID NO: 4, which is filed herewith by electronic submission and is incorporated by reference herein:

SEQ ID 1: Synthetic nucleotide sequence coding for a protein having the activity of a glutamine:fructose-6-phosphate-amidotransferase (GFAT) from *E. coli*. The sequence is optimized for expression in cotton plant cells. The nucleotide sequence shown codes for a polypeptide having the amino acid sequence of SEQ ID 2.

SEQ ID 2: Amino acid sequence of a polypeptide having the activity of a glutamine:fructose-6-phosphate-amidotransferase (GFAT) from *E. coli*. The amino acid sequence shown can be derived from SEQ ID 1.

SEQ ID 3: T-DNA of pTDBI 252. It comprises a nucleotide sequence according to SEQ ID 1 encoding a GFAT polypeptide from *E. coli* under control of a fiber-selective SCW-PRP promotor, a DNA region encoding a NOD C chitin synthase under control of a fiber-selective SCW-PRP promotor and the epsps gene as a selectable marker.

SEQ ID 4: T-DNA of pTDBI 250. It comprises a nucleotide sequence according to SEQ ID 1 encoding a GFAT polypeptide from *E. coli* under control of a fiber-selective Fb8-like-1 promotor, a DNA region encoding a NOD C chitin synthase under control of a fiber-selective Fb8-like-1 promotor and the epsps gene as a selectable marker.

EXAMPLES

Example 1

Construction of a Chimeric Gene Encoding a Glutamine:Fructose-6-Phosphate-Amidotransferase (GFAT) Protein for Expression in Cotton Cells A DNA molecule having the nucleic acid sequence according to SEQ ID 1 was synthesized by Entelechon GmbH. The nucleotide sequence was designed i) to encode a polypeptide according to SEQ ID 2 and ii) to optimize the nucleotide sequence for expression in cotton plant cells. For this purpose, factors such as codon usage, mRNA secondary structure, the AT content, cryptic splice sites or restriction sites were taken into account.

The resulting nucleotide sequence as disclosed in SEQ ID 1 is 75% identical (1390 matching bases out of 1830) to the published nucleotide sequence encoding a GFAT protein from E. coli which was adapted to the codon usage in plants (WO 2007/039314).

Using standard recombinant DNA techniques, the following chimeric GFAT gene was constructed: A chimeric glutamine-6-phosphate-amidotransferase gene comprising the following operably linked DNA regions:
i. the fiber-selective SCW-PRP promoter region according to the sequence from nucleotide position 61 to 1499 of SEQ ID 3,
ii. a DNA fragment coding for the 35 N-terminal amino acids of ▯ a DNA xylosyltransferase from *Arabidopsis thaliana* which function as a Golgi localization signal peptide,
iii. a DNA fragment coding for NOD C of *Azorhizobium caulinodans* cloned in frame with the previous DNA fragment,
iv. the 3' untranslated sequence of the 35S transcript of the Cauliflower Mosaic Virus,
v. the fiber-selective SCW-PRP promoter region according to the sequence from nucleotide position 61 to 1499 of SEQ ID 3,
vi. a DNA region having the nucleotide sequence according to SEQ ID 1 encoding a glutamine: fructose-6-phosphate amidotransferase from *E. coli* according to SEQ ID 2,
vii. the 3' untranslated sequence of histone H4 gene of *Arabidopsis thaliana*.

This chimeric gene was introduced between T-DNA borders of a T-DNA vector together with a chimeric double mutated 5-enol-pyruvylshikimate-3-phosphate synthase (epsps) gene from *Zea mays* (corn) providing resistance to N-(phosphonomethyl)glycin as a selectable marker. The resulting T-DNA vector was named pTDBI 252. The sequence of the T-DNA of this vector is provided in SEQ ID 3. The genetic elements of the T-DNA of this vector are represented in Table 1.

Another chimeric GFAT gene was constructed containing the following operably linked DNA regions:
i. the fiber-selective Fb8-like-1 promoter region according to the sequence from nucleotide position 60 to 1495 of SEQ ID 4,
ii. a DNA fragment coding for the 35 N-terminal amino acids of ▯ a DNA xylosyltransferase from *Arabidopsis thaliana* which serves as a Golgi localization peptide,
iii. a DNA fragment coding for NOD C of *Azorhizobium caulinodans* cloned in frame with the previous DNA fragment,
iv. the 3' untranslated sequence of the 35S transcript of the Cauliflower Mosaic Virus,
v. the fiber-selective Fb8-like-1 promoter region according to the sequence from nucleotide position 60 to 1495 of SEQ ID 4,
vi. a DNA region having the nucleotide sequence according to SEQ ID 1 encoding a glutamine: fructose-6-phosphate amidotransferase from *E. coli* according to SEQ ID 2,
vii. the 3' untranslated sequence of histone H4 gene of *Arabidopsis thaliana*.

This chimeric gene was introduced between T-DNA borders of a T-DNA vector together with a chimeric epsps gene as a selectable marker. The resulting T-DNA vector was named pTDBI 250, The sequence of the T-DNA of this vector is provided in SEQ ID 4. The genetic elements of the T-DNA are represented in Table 2.

TABLE 1

Elements of the T-DNA of pTDBI 252

| Start | End | Name | Description |
|---|---|---|---|
| 1 | 25 | RB | Right border repeat from the T-DNA of *Agrobacterium tumefaciens* |
| 61 | 1499 | PSCW-PRP | sequence including the promoter region of a proline-rich cell wall protein gene of *Gossypium hirsutum* |
| 1503 | 1607 | RPXylTAt | coding sequence for the Golgi retention peptide of the beta-1,2-xylosyltransferase gene of *A. thaliana* |
| 1608 | 2798 | NodC | coding sequence of the N-acetylglucosaminyltransferase gene NodC of *Azorhizobium caulinodans* |
| 2810 | 3030 | 3'35S | sequence including the 3' untranslated region of the 35S transcript of the Cauliflower Mosaic Virus |
| 3068 | 4506 | PSCW-PRP | sequence including the promoter region of a proline-rich cell wall protein gene of *Gossypium hirsutum* |
| 4510 | 6339 | GFAT | coding region of the glutamine:fructose-6-phosphate amidotransferase gene of *Escherichia coli* optimized for expression in cotton plant cells |
| 6357 | 7017 | 3'H4 At | sequence including the 3' untranslated region of the histone H4 gene of *Arabidopsis thaliana* |
| 7067 | 7983 | PH4 | sequence including the promoter region of the histone H4 gene of *Arabidopsis thaliana* |
| 8017 | 8497 | intron1 H3At + flanking region | sequence including the first intron of gene II of the histone H3.III variant of *Arabidopsis thaliana* |
| 8502 | 8873 | TP_opt | coding sequence of the optimized transit peptide, containing sequence of the RuBisCO small subunit genes of *Zea mays* (corn) and *Helianthus annuus* |
| 8874 | 10211 | 2mepsps | coding sequence of the double-mutant 5-enol-pyruvylshikimate-3-phosphate synthase gene of *Zea mays* (corn) |

TABLE 1-continued

Elements of the T-DNA of pTDBI 252

| Start | End | Name | Description |
|---|---|---|---|
| 10235 | 10895 | 3'H4 At | sequence including the 3' untranslated region of the histone H4 gene of *Arabidopsis thaliana* |
| 11008 | 11032 | LB | Left border repeat from the T-DNA of *Agrobacterium tumefaciens* |

TABLE 2

Elements of pTDBI 250

| Start | End | Name | Description |
|---|---|---|---|
| 1 | 25 | RB | Right border repeat from the T-DNA of *Agrobacterium tumefaciens* |
| 60 | 1495 | Pfb8-like-1 | sequence including the promoter region of the fb8-like gene of *Gossypium hirsutum* (cotton) |
| 1497 | 1601 | RPxylTAt | coding sequence for the Golgi retention peptide of the beta-1,2-xylosyltransferase gene of *Arabidopsis thaliana* |
| 1602 | 2792 | NodC | coding sequence of the N-acetylglucosaminyl-transferase gene nodC of *Azorhizobium caulinodans* |
| 2804 | 3026 | 3'35S | sequence including the 3' untranslated region of the 35S transcript of the Cauliflower Mosaic Virus |
| 3061 | 4496 | Pfb8-like-1 | sequence including the promoter region of the fb8-like gene of *Gossypium hirsutum* (cotton) |
| 4498 | 6327 | GFAT | coding region of the glutamine:fructose-6-phosphate amidotransferase gene of *Escherichia coli* optimized for expression in cotton plant cells |
| 6345 | 7005 | 3'H4 At | sequence including the 3' untranslated region of the histone H4 gene of *Arabidopsis thaliana* |
| 7056 | 7970 | PH4 AT | sequence including the promoter region of the histone H4 gene of *Arabidopsis thaliana* |
| 8005 | 8486 | intron1 H3At + flanking region | sequence including the first intron of gene II of the histone H3.III variant of *Arabidopsis thaliana* |
| 8490 | 8861 | TP_opt | coding sequence of the optimized transit peptide, containing sequence of the RuBisCO small subunit genes of *Zea mays* (corn) and *Helianthus annuus* |
| 8862 | 10199 | 2mepsps | coding sequence of the double-mutant 5-enol-pyruvylshikimate-3-phosphate synthase gene of *Zea mays* (corn) |
| 10223 | 10883 | 3'H4 At | sequence including the 3' untranslated region of the histone H4 gene of *Arabidopsis thaliana* |
| 10996 | 11020 | LB | Left border repeat from the T-DNA of *Agrobacterium tumefaciens* |

As a control a chimeric gene was used containing the following operably linked DNA regions:

i. the fiber-selective SCW-PRP promoter region according to the sequence from nucleotide position 61 to 1499 of SEQ ID 3,
ii. a DNA fragment coding for the 35 N-terminal amino acids of [ a DNA xylosyltransferase from *Arabidopsis thaliana*,
iii. a DNA fragment coding for NOD C of *Azorhizobium caulinodans* cloned in frame with the previous DNA fragment,
iv. the 3' untranslated sequence of the 35S transcript of the Cauliflower Mosaic Virus,
v. the fiber-selective SCW-PRP promoter region according to the sequence from nucleotide position 61 to 1499 of SEQ ID 3,
vi. a DNA region encoding a glutamine:fructose-6-phosphate amidotransferase from *E. coli* which was optimized for codon usage in plants as described in WO 2007/039314 under SEQ ID 10 therein,
vii. the 3' untranslated sequence of histone H4 gene of *Arabidopsis thaliana*.

This chimeric gene was introduced between T-DNA borders of a T-DNA vector together with a chimeric epsps gene as a selectable marker. The resulting T-DNA vector was named pTGK 110, This vector is identical to pTDBI252 except for the GFAT encoding sequence.

Example 2

Generation of Transgenic Cotton Plants Expressing a Glutamine: Fructose-6-Phosphate Amidotransferase The T-DNA vectors were introduced into *Agrobacterium tumefaciens* strains containing a helper Ti-plasmid and used in cotton transformation essentially as described in WO00/71733. T0 plants were further analyzed as described in Example 3.

Example 3

Determination of the Glucosamine Content of Cotton Fibers

Fibers from transgenic cotton T0 plants were isolated, treated with trifluoroacetic acid (TFA) to hydrolyze the glucosamine polymers and analyzed for the glucosamine content by HPLC. All steps were carried out following standard protocols.

Fibers of untransformed lines contained about 0.01% of GlcN. The results for the measured glucosamine content of cotton fibers from different T0 plants expressing the GFAT gene according to the invention under the control of the SCW-PRP promotor (transformed with pTDBI 252) are depicted in Table 3.

TABLE 3

GlcN content of cotton fibers from individual T0 plants

| GFAT optimized (pTDBI 252) | | GFAT control (pTGK 110) | |
|---|---|---|---|
| pl1 | 0.0115 * | cpl1 | 0.0101 * |
| pl2 | 0.0118 * | cpl2 | 0.0112 * |
| pl3 | 0.0136 * | cpl3 | 0.0120 * |
| pl4 | 0.0141 * | cpl4 | 0.0121 * |
| pl5 | 0.0318 | cpl5 | 0.0125 * |
| pl6 | 0.0340 | cpl6 | 0.0316 |
| pl7 | 0.0371 | cpl7 | 0.0330 |
| pl8 | 0.0389 | cpl8 | 0.0334 |
| pl9 | 0.0401 | cpl9 | 0.0349 |
| pl10 | 0.0405 | cpl10 | 0.0425 |
| pl11 | 0.0431 | cpl11 | 0.0446 |
| pl12 | 0.0448 | cpl12 | 0.0536 |
| pl13 | 0.0472 | cpl13 | 0.0546 |
| pl14 | 0.0502 | cpl14 | 0.0566 |
| pl15 | 0.0530 | cpl15 | 0.0589 |
| pl16 | 0.0538 | cpl16 | 0.0597 |
| pl17 | 0.0558 | cpl17 | 0.0599 |
| pl18 | 0.0630 | cpl18 | 0.0714 |
| pl19 | 0.0674 | Average: | 0.0385 |
| pl20 | 0.0762 | | |
| pl21 | 0.0783 | | |
| pl22 | 0.0811 | | |
| pl23 | 0.0817 | | |
| pl24 | 0.0910 | | |
| pl25 | 0.0929 | | |
| pl26 | 0.0965 | | |
| Pl27 | 0.1016 | | |
| pl28 | 0.1152 | | |
| pl29 | 0.1243 | | |
| pl30 | 0.1319 | | |
| Average: | 0.0607 | | |

Values represent % GlcN of total fiber weight;
* considered as background

The numbers given represent % GlcN of total fiber weight. Values below 0.015 were considered as background. Table 3 also shows the GlcN content found in fibers from individual T0 cotton plants that were transformed with the control vector pTGK 110 which comprises a GFAT encoding DNA region which is optimized for codon usage in plants and is known in the art.

Table 4 shows the average and maximum GlcN content (measured in % of total fiber weight) of cotton fibers derived from T0 plants expressing either the GFAT gene according to the invention under control of the SCW-PRP promotor or under the control of the Fb8-like-1 promotor. As a control values are given for plants expressing the plant-optimized GFAT gene described in WO 2007/039314. The mean GlcN content of fibers expressing the GFAT gene sequence according to SEQ ID 1 under control of the SCW-PRP promotor was about four times above background level (0.061% vs. 0.015%) and nearly twice that of control plants expressing a plant-optimized GFAT gene sequence published in WO 2007/039314 (0.061% vs. 0.039%). The maximum GlcN content that was measured in a T0 plant expressing the GFAT gene according to the invention under control of the SCW-PRP promotor was nearly 10-fold above the background level of fibers from plants not expressing an artificially introduced gene construct (0.132% vs. 0.015%). Moreover, it was nearly twice that of control plants expressing a plant-optimized GFAT gene sequence published in WO 2007/039314 (0.132% vs. 0.071%). Likewise, plants expressing a GFAT gene according to SEQ ID 1 under the control of the Fb8-like-1 promoter had a maximum increase in the GlcN content of the fibers by more than 10-fold (0.178% vs. 0.015%) and a mean 2-fold increase in the GlcN content of the fibers (0.039% vs. 0.015%) compared to plants not expressing an artificially introduced gene construct.

TABLE 4

Mean and average GlcN content of fibers from T0 cotton plants expressing a GFAT gene according to SEQ ID 1 under the control of different fiber-selective promotors)

| Promoter | GFAT ctrl. average | GFAT ctrl. max. | GFAT opt. average | GFAT opt. maximum |
|---|---|---|---|---|
| SCW-PRP | 0.039 | 0.071 | 0.061 | 0.132 |
| Fb8-like-1 | | | 0.039 | 0.178 |

Values represent % GlcN of total fiber weight

Example 4

Cotton Fibers With Increased Reactivity

Transgenic cotton plants comprising a chimeric GFA gene and a chimeric NOD C gene operably linked to a fiber-specific promoter as outlined in Example 1 are generated as described in Example 2. Mature cotton fibers are harvested from these plants and can be stained with anionic dyes such as Congo Red or can be reacted with wheat germ agglutinin (WGA) coupled Alexa fluor 555. WGA specifically binds to N-acetylglucosamine in plant cells and therefore can be used as a detection reagent for N-acetylglucosamine. In addition, the resulting mature cotton fibers can be stained with commercial dyes including cotton reactive dyes (e.g. Reactive Red 120, Levafix Blue CA), acid dyes (Acid Orange 7, Acid Blue 281) and wool reactive dyes (e.g. Reactive Red 116, Realan Amber EHF).

The invention claimed is:

1. A cotton plant cell comprising a chimeric gene comprising the following operably linked DNA regions:
   a) a plant-expressible promotor,
   b) a DNA region coding for a GFAT polypeptide wherein said GFAT is encoded by a nucleotide sequence comprising
      i) a nucleotide sequence according to SEQ ID NO: 1,
      ii) or a variant thereof, wherein one or more nucleotides differ from the nucleotide sequence according to SEQ ID NO: 1, provided that said variant differs in no more than 20 nucleotides from SEQ ID NO: 1, which encodes a glutamine:fructose-6-phosphate-amidotransferase (GFAT) according to SEQ ID NO: 2
      iii) or a complementary sequence of i) or ii)), and
   c) optionally a DNA region involved in transcription termination and polyadenylation
   wherein said cotton plant cell additionally comprises a second chimeric gene comprising the following operably linked DNA regions:
   a) a plant-expressible promotor,
   b) a DNA sequence coding for a chitin synthase polypeptide and
   c) optionally a DNA region involved in transcription termination and polyadenylation.

2. A cotton plant cell according to claim 1 wherein said chitin synthase is an N-acetylglucosamine transferase of the Nod C type.

3. A cotton plant cell according to claim 2 wherein said chitin synthase polypeptide comprises a Golgi localization signal.

4. A cotton plant consisting of plant cells according to claim 1.

5. A method for producing cotton fibers with positively charged polysaccharides, such as oligo-N-acetylglucosamines or oligo-glucosamines, comprising the steps of
   i) expressing a chimeric gene comprising the following operably linked DNA regions:
      a) a plant-expressible promotor,
      b) a DNA region coding for a GFAT polypeptide wherein said GFAT is encoded by a nucleotide sequence comprising
         i) a nucleotide sequence according to SEQ ID NO: 1,
         ii) or a variant thereof, wherein one or more nucleotides differ from the nucleotide sequence according to SEQ ID NO: 1, provided that said variant litters in no more than 20 nucleotides from SEQ ID NO: 1, which encodes a glutamine:fructose-6-phosphate-amidotransferase (GFAT) according to SEQ ID NO: 2
         iii) or a complementary sequence of i) or ii)), and
      c) optionally a DNA region involved in transcription termination and polyadenylation
   and expressing a second chimeric gene comprising
      a) a plant-expressible promotor,
      b) a DNA sequence coding for a chitin synthase polypeptide and
      c) optionally a DNA region involved in transcription termination and polyadenylation
   in a cotton plant cell,
   ii) regenerating a cotton plant from cotton plant cells of step i) and
   iii) optionally isolating fibers from said cotton plant.

6. The cotton plant cell according to claim 1, wherein said plant-expressible promotor is a fiber-preferential promotor.

7. The method according to claim 5, wherein said plant-expressible promotor is a fiber-preferential promotor.

* * * * *

SEQUENCE LISTING

```
<160> NUMBER OF SEQ ID NOS: 4

<210> SEQ ID NO 1
<211> LENGTH: 1830
<212> TYPE: DNA
<213> ORGANISM: artificial
<220> FEATURE:
<223> OTHER INFORMATION: artificial sequence encoding the
      glutamine:fructose-6-phosphate-amidotransferase (GFAT) of E. coli
<220> FEATURE:
<221> NAME/KEY: CDS
<222> LOCATION: (1)..(1830)
```

```
<400> SEQUENCE: 1 atg tgc gga att gtt ggc gca ata gca caa agg gac gta gca gaa atc    48
Met Cys Gly Ile Val Gly Ala Ile Ala Gln Arg Asp Val Ala Glu Ile
1               5                   10                  15 ctt ctt gaa gga ctc cgt cgt ctg gaa tac aga gga tat gat tct gcc    96
Leu Leu Glu Gly Leu Arg Arg Leu Glu Tyr Arg Gly Tyr Asp Ser Ala
            20                  25                  30 ggt cta gcc gtt gta gat gcc gaa ggt cac atg aca cgt cta aga cgt   144
Gly Leu Ala Val Val Asp Ala Glu Gly His Met Thr Arg Leu Arg Arg
        35                  40                  45 ctg ggt aag gtt caa atg ctg gct caa gca gcc gaa gaa cat cct tta   192
Leu Gly Lys Val Gln Met Leu Ala Gln Ala Ala Glu Glu His Pro Leu
50                  55                  60 cat ggt ggc aca ggt att gct cac act aga tgg gct act cac ggt gaa   240
His Gly Gly Thr Gly Ile Ala His Thr Arg Trp Ala Thr His Gly Glu
65                  70                  75                  80 cct tca gag gta aat gct cat cca cat gtc tct gag cac att gtg gtc   288
Pro Ser Glu Val Asn Ala His Pro His Val Ser Glu His Ile Val Val
                85                  90                  95 gtt cac aac ggg atc atc gaa aac cat gaa cca ctt cga gaa gag ctg   336
Val His Asn Gly Ile Ile Glu Asn His Glu Pro Leu Arg Glu Glu Leu
            100                 105                 110 aaa gct cgt ggc tat act ttc gtt tca gag aca gac act gag gtg att   384
Lys Ala Arg Gly Tyr Thr Phe Val Ser Glu Thr Asp Thr Glu Val Ile
        115                 120                 125 gct cat ctc gtg aac tgg gaa ctg aaa caa ggg gga act ctg aga gag   432
Ala His Leu Val Asn Trp Glu Leu Lys Gln Gly Gly Thr Leu Arg Glu
    130                 135                 140 gct gtt cta cgt gct atc cct caa tta cgt ggt gct tac ggg aca gtg   480
Ala Val Leu Arg Ala Ile Pro Gln Leu Arg Gly Ala Tyr Gly Thr Val
145                 150                 155                 160 atc atg gat tca aga cac cca gat aca ctg ctg gca gca agg tct ggt   528
Ile Met Asp Ser Arg His Pro Asp Thr Leu Leu Ala Ala Arg Ser Gly
                165                 170                 175 agt cca ctg gtg att gga ctg ggg atg gga gaa aac ttt atc gct tcg   576
Ser Pro Leu Val Ile Gly Leu Gly Met Gly Glu Asn Phe Ile Ala Ser
            180                 185                 190 gat caa ctg gct ctg tta cct gtg aca cgg aga ttt atc ttc ctt gaa   624
Asp Gln Leu Ala Leu Leu Pro Val Thr Arg Arg Phe Ile Phe Leu Glu
        195                 200                 205 gag ggc gat atc gcg gaa ata act cga cgt agc gta aac atc ttc gat   672
Glu Gly Asp Ile Ala Glu Ile Thr Arg Arg Ser Val Asn Ile Phe Asp
    210                 215                 220 aaa acc gga gca gaa gta aaa cgc cag gat atc gaa tcc aat ctt caa   720
Lys Thr Gly Ala Glu Val Lys Arg Gln Asp Ile Glu Ser Asn Leu Gln
225                 230                 235                 240 tac gac gcc ggc gat aaa ggc ata tac cga cac tac atg cag aaa gag   768
Tyr Asp Ala Gly Asp Lys Gly Ile Tyr Arg His Tyr Met Gln Lys Glu
                245                 250                 255 atc tac gag caa ccg aac gct atc aag aat acc ctt act ggg cgt atc   816
Ile Tyr Glu Gln Pro Asn Ala Ile Lys Asn Thr Leu Thr Gly Arg Ile
            260                 265                 270 tca cat ggt cag gtt gac tta tct gaa ctg gga cca aac gca gac gaa   864
Ser His Gly Gln Val Asp Leu Ser Glu Leu Gly Pro Asn Ala Asp Glu
        275                 280                 285 cta ctg tcg aag gta gaa cat att cag atc ctc gcg tgt ggt act tct   912
Leu Leu Ser Lys Val Glu His Ile Gln Ile Leu Ala Cys Gly Thr Ser
    290                 295                 300
```

```
tat aac tct ggt atg gtc agt cgc tat tgg ttt gaa tca ctg gca gga      960
Tyr Asn Ser Gly Met Val Ser Arg Tyr Trp Phe Glu Ser Leu Ala Gly
305             310                 315                 320 att cct tgc gac gtc gaa att gcc tcg gaa ttc aga tat cgc aag tct     1008
Ile Pro Cys Asp Val Glu Ile Ala Ser Glu Phe Arg Tyr Arg Lys Ser
                325                 330                 335 gca gta aga cgc aac agc ctg atg ata acg tta tct cag tct gga gaa     1056
Ala Val Arg Arg Asn Ser Leu Met Ile Thr Leu Ser Gln Ser Gly Glu
                340                 345                 350 acg gct gat aca ctg gct gga tta cgt ctg tca aaa gag ctt ggc tac     1104
Thr Ala Asp Thr Leu Ala Gly Leu Arg Leu Ser Lys Glu Leu Gly Tyr
            355                 360                 365 ctt ggt tct cta gca atc tgt aac gtt cct ggt agc tct ctt gtg cga     1152
Leu Gly Ser Leu Ala Ile Cys Asn Val Pro Gly Ser Ser Leu Val Arg
        370                 375                 380 gaa tct gat ctt gct ctt atg act aac gct gga aca gaa atc ggg gtg     1200
Glu Ser Asp Leu Ala Leu Met Thr Asn Ala Gly Thr Glu Ile Gly Val
385                 390                 395                 400 gca tcc aca aaa gca ttt aca act caa ctt acg gtg ctg cta atg ctt     1248
Ala Ser Thr Lys Ala Phe Thr Thr Gln Leu Thr Val Leu Leu Met Leu
                405                 410                 415 gtg gca aag ctg tct aga ctc aaa ggt cta gat gcc tcc atc gag cat     1296
Val Ala Lys Leu Ser Arg Leu Lys Gly Leu Asp Ala Ser Ile Glu His
                420                 425                 430 gat atc gtt cat ggt ctg caa gct ctt cct agc cga att gag cag atg     1344
Asp Ile Val His Gly Leu Gln Ala Leu Pro Ser Arg Ile Glu Gln Met
            435                 440                 445 ctg tca caa gac aaa agg att gaa gcc ctg gca gaa gat ttc tca gac     1392
Leu Ser Gln Asp Lys Arg Ile Glu Ala Leu Ala Glu Asp Phe Ser Asp
        450                 455                 460 aag cat cac gct ttg ttt ctc ggt cgt ggc gat cag tat cct atc gct     1440
Lys His His Ala Leu Phe Leu Gly Arg Gly Asp Gln Tyr Pro Ile Ala
465                 470                 475                 480 ctc gaa ggc gca ttg aag ctc aaa gag atc tcc tat ata cac gct gaa     1488
Leu Glu Gly Ala Leu Lys Leu Lys Glu Ile Ser Tyr Ile His Ala Glu
                485                 490                 495 gct tac gct gca ggc gaa ctg aaa cac gga cct cta gct ctt att gac     1536
Ala Tyr Ala Ala Gly Glu Leu Lys His Gly Pro Leu Ala Leu Ile Asp
                500                 505                 510 gca gat atg ccc gtt atc gtc gtt gca cca aac aac gaa ttg ctg gag     1584
Ala Asp Met Pro Val Ile Val Val Ala Pro Asn Asn Glu Leu Leu Glu
            515                 520                 525 aag ctg aaa tca aat att gaa gag gta cgt gca aga ggc gga caa ctt     1632
Lys Leu Lys Ser Asn Ile Glu Glu Val Arg Ala Arg Gly Gly Gln Leu
        530                 535                 540 tat gtc ttc gct gag caa gat gcc ggt ttt gta agt agc gat aac atg     1680
Tyr Val Phe Ala Glu Gln Asp Ala Gly Phe Val Ser Ser Asp Asn Met
545                 550                 555                 560 cac atc atc gag atg cct cac gtg gaa gag gtg att gct ccg atc ttc     1728
His Ile Ile Glu Met Pro His Val Glu Glu Val Ile Ala Pro Ile Phe
                565                 570                 575 tac aca gtt ccc ctg cag ctt ctg gct tat cac gtt gcc ctt atc aaa     1776
Tyr Thr Val Pro Leu Gln Leu Leu Ala Tyr His Val Ala Leu Ile Lys
                580                 585                 590 gga act gac gtt gac cag cca agg aat ctc gca aag tca gta acg gtt     1824
Gly Thr Asp Val Asp Gln Pro Arg Asn Leu Ala Lys Ser Val Thr Val
            595                 600                 605 gag taa                                                             1830
Glu
```

<210> SEQ ID NO 2
<211> LENGTH: 609
<212> TYPE: PRT
<213> ORGANISM: artificial
<220> FEATURE:
<223> OTHER INFORMATION: Synthetic Construct

<400> SEQUENCE: 2

```
Met Cys Gly Ile Val Gly Ala Ile Ala Gln Arg Asp Val Ala Glu Ile
1               5                   10                  15

Leu Leu Glu Gly Leu Arg Arg Leu Glu Tyr Arg Gly Tyr Asp Ser Ala
            20                  25                  30

Gly Leu Ala Val Val Asp Ala Glu Gly His Met Thr Arg Leu Arg Arg
        35                  40                  45

Leu Gly Lys Val Gln Met Leu Ala Gln Ala Ala Glu Glu His Pro Leu
    50                  55                  60

His Gly Gly Thr Gly Ile Ala His Thr Arg Trp Ala Thr His Gly Glu
65                  70                  75                  80

Pro Ser Glu Val Asn Ala His Pro His Val Ser Glu His Ile Val Val
                85                  90                  95

Val His Asn Gly Ile Ile Glu Asn His Glu Pro Leu Arg Glu Glu Leu
            100                 105                 110

Lys Ala Arg Gly Tyr Thr Phe Val Ser Glu Thr Asp Thr Glu Val Ile
        115                 120                 125

Ala His Leu Val Asn Trp Glu Leu Lys Gln Gly Gly Thr Leu Arg Glu
    130                 135                 140

Ala Val Leu Arg Ala Ile Pro Gln Leu Arg Gly Ala Tyr Gly Thr Val
145                 150                 155                 160

Ile Met Asp Ser Arg His Pro Asp Thr Leu Leu Ala Ala Arg Ser Gly
                165                 170                 175

Ser Pro Leu Val Ile Gly Leu Gly Met Gly Glu Asn Phe Ile Ala Ser
            180                 185                 190

Asp Gln Leu Ala Leu Leu Pro Val Thr Arg Arg Phe Ile Phe Leu Glu
        195                 200                 205

Glu Gly Asp Ile Ala Glu Ile Thr Arg Arg Ser Val Asn Ile Phe Asp
    210                 215                 220

Lys Thr Gly Ala Glu Val Lys Arg Gln Asp Ile Glu Ser Asn Leu Gln
225                 230                 235                 240

Tyr Asp Ala Gly Asp Lys Gly Ile Tyr Arg His Tyr Met Gln Lys Glu
                245                 250                 255

Ile Tyr Glu Gln Pro Asn Ala Ile Lys Asn Thr Leu Thr Gly Arg Ile
            260                 265                 270

Ser His Gly Gln Val Asp Leu Ser Glu Leu Gly Pro Asn Ala Asp Glu
        275                 280                 285

Leu Leu Ser Lys Val Glu His Ile Gln Ile Leu Ala Cys Gly Thr Ser
    290                 295                 300

Tyr Asn Ser Gly Met Val Ser Arg Tyr Trp Phe Glu Ser Leu Ala Gly
305                 310                 315                 320

Ile Pro Cys Asp Val Glu Ile Ala Ser Glu Phe Arg Tyr Arg Lys Ser
                325                 330                 335

Ala Val Arg Arg Asn Ser Leu Met Ile Thr Leu Ser Gln Ser Gly Glu
            340                 345                 350

Thr Ala Asp Thr Leu Ala Gly Leu Arg Leu Ser Lys Glu Leu Gly Tyr
        355                 360                 365
```

Leu Gly Ser Leu Ala Ile Cys Asn Val Pro Gly Ser Ser Leu Val Arg
      370                 375                 380

Glu Ser Asp Leu Ala Leu Met Thr Asn Ala Gly Thr Glu Ile Gly Val
385                 390                 395                 400

Ala Ser Thr Lys Ala Phe Thr Thr Gln Leu Thr Val Leu Leu Met Leu
                405                 410                 415

Val Ala Lys Leu Ser Arg Leu Lys Gly Leu Asp Ala Ser Ile Glu His
            420                 425                 430

Asp Ile Val His Gly Leu Gln Ala Leu Pro Ser Arg Ile Glu Gln Met
        435                 440                 445

Leu Ser Gln Asp Lys Arg Ile Glu Ala Leu Ala Glu Asp Phe Ser Asp
450                 455                 460

Lys His His Ala Leu Phe Leu Gly Arg Gly Asp Gln Tyr Pro Ile Ala
465                 470                 475                 480

Leu Glu Gly Ala Leu Lys Leu Lys Glu Ile Ser Tyr Ile His Ala Glu
                485                 490                 495

Ala Tyr Ala Ala Gly Glu Leu Lys His Gly Pro Leu Ala Leu Ile Asp
            500                 505                 510

Ala Asp Met Pro Val Ile Val Ala Pro Asn Asn Glu Leu Leu Glu
        515                 520                 525

Lys Leu Lys Ser Asn Ile Glu Glu Val Arg Ala Arg Gly Gly Gln Leu
530                 535                 540

Tyr Val Phe Ala Glu Gln Asp Ala Gly Phe Val Ser Ser Asp Asn Met
545                 550                 555                 560

His Ile Ile Glu Met Pro His Val Glu Val Ile Ala Pro Ile Phe
                565                 570                 575

Tyr Thr Val Pro Leu Gln Leu Leu Ala Tyr His Val Ala Leu Ile Lys
            580                 585                 590

Gly Thr Asp Val Asp Gln Pro Arg Asn Leu Ala Lys Ser Val Thr Val
        595                 600                 605

Glu

<210> SEQ ID NO 3
<211> LENGTH: 11032
<212> TYPE: DNA
<213> ORGANISM: Artificial
<220> FEATURE:
<223> OTHER INFORMATION: T-DNA of pTDBI 252

<400> SEQUENCE: 3
aattacaacg gtatatatcc tgccagtact gggccccctc gagggcgatc gcgcggccgc    60
ttcacggaaa gttgttatat ataagttcag taaataataa tgaaatataa attttaatta   120
tatctagtac tcaataagaa gatggagaaa gttatgttaa ttatagttat aaattattta   180
taaatttaat atatatatat aaagaaaata gttgtataac taataattat ttttacaata   240
ctttatatag ttatatttaa aaaaatttta aaattaaaat actattattt tgttcaatat   300
attaatattt atattattta atttattatt gaatatgaat aaatttttt tgaaaattat   360 attttaatt tttagaaatt ttatataact ttccatatat atatttctga tttgtcaatt   420
tcttttgaga tttatctaaa ttgatttgaa ttttttttat ttttaaaaaa taaaataatt   480
ttaaaatttc ttggaatttt atataaattt ttggattttt caaaaaaaat tgagattttt   540 ttctttttt tcgattttt aaatttattt caggaaaata taaactaact tttctttgct   600
ttgggtataa ttaatattag ataacccaca aattagatca ataggagctt catgtcctaa   660

```
tcccatttaa ttacttttgt tgtatcatta atttagtcga ccttacatag tagctctatg      720
gggcaaatag ttataaatgt taaattagta tttaaatctt gaagttttta atttaaagtt      780
cagactatta gtattatatc aaatatttaa gggtaaatat atattctaat atctaagctt      840
gggtcaaggt ttaaattaag tacttaaact tggttttata gttcaaattg atttaaataa      900
ctaagtatta atttgaatta agaagcaaag ttcaagtacc taattagact ataaaaaaaa      960
cttttgctag taaattgaac cttaaagtcg agtttagtta tctaattgga caaaaaatc     1020 ttaaatacca atttaaaccc taaagtcaag tttaggtacc aaagtgtata tttatctaat     1080
atttaaattt gatccaccta atttaaattt ttttggtcca atgcaataag agaattaatt     1140
aatacttaca cacatgatag agatataccc acaacagata cacactacaa aaaacattaa     1200
aaaatagaaa gatatatttc ctacaaaatt taaaagcatt taatttttta actaacatta     1260
gacaaatgga aatggaaaga cttattttta agtttatgga tgaatctaat ttatctaaac     1320
attgggtttt ttttttttgt gacgaaatat gggtgagaga aggtagtaag ctaagtaggg     1380
gagtaatatc tcaaacaaat aattaaaaaa ctcctttaaa tgtggctata aatacctgaa     1440
accaatcctt cttcctcaa ctcaaatctt caatctttag atcatctctc caaaaaaata     1500
ccatgagtaa acggaatccg aagattctga agattttct gtatatgtta cttctcaact     1560
ctctctttct catcatctac ttcgttttc actcatcgtc gttttcaagt gtcgtagatg     1620
tgatcggttt gcttgcgact gcagcctacg tgacgttggc gagcgcatac aaggtggtcc     1680
agttcattaa cgtgtcgagc gtaacggatg tcgctggtct cgaaagtgat gctttgccgc     1740
tcactccaag ggttgacgtt atcgtgccga cattcaatga gaactccagc acattgctcg     1800
agtgcgtcgc ttctatatgc gcacaagact accgcggacc aataacgatt gtcgtggtag     1860
acgatgggtc gaccaacaaa acatcatttc acgcagtatg cgacaagtac gcgagcgacg     1920
aaaggttcat atttgtcgaa cttgatcaaa acaagggaa gcgcgccgcg caaatggagg     1980
ccatcaggag aacagacgga gacctgatac taaacgtaga ctcggacacg gttatagata     2040
aggatgttgt tacaaagctt gcgtcgtcca tgagagcccc gaatgtcggt ggtgtcatgg     2100
ggcagctcgt tgcaaagaat cgagaaagat cttggcttac cagattaatc gatatggagt     2160 actgcttgc gtgtaacgag gagcgcattg cgcagtcgag gtttggctcc gtgatgtgtt     2220
gttgtgggcc gtgcgccatg tatagaagat ctgcaattac gccactattg gcagaatatg     2280
agcaccagac attcctaggg cgtccgagca actttggtga ggatcgccat ctcacaatcc     2340
tgatgctgaa ggcgggattt cggaccgggt acgtcccagg tgccgtagcg aggacgttgg     2400
ttccggatgg gctggcgccg tacctgcgcc agcaactccg ctgggcccgc agcacttatc     2460
gcgacaccgc cctcgcctta cgtataaaga aaaatctaag caaatatatc acctttgaga     2520
tatgcgcaca gaatttgggt acggctctct tacttgtgat gaccatgatt tcgctttcgc     2580
tgactacatc agggtcgcaa acgcccgtta tcattctggg tgtcgttgtg gggatgtcta     2640
taataagatg ttgttctgtc gcccttatag cgaaagattt tcggtttcta tacttcatcg     2700
ttcactcagc gttgaatgtt ctaatttta cgccgttaaa actctatgcc ctgttaacca     2760
ttcgggatag tcgtggcta tcacgcgaga gttcctaagc tagcaagctt ggacacgctg     2820
aaatcaccag tctctctcta caaatctatc tctctctatt ttctccataa taatgtgtga     2880
gtagttccca gataagggaa ttagggtcc tatagggttt cgctcatgtg ttgagcatat     2940
aagaaaccct tagtatgtat ttgtatttgt aaaatacttc tatcaataaa atttctaatt     3000 cctaaaaacca aaatccagta ctaaaatcca gacgcgtcct gcaggcccgg gttaattaag     3060
```

```
cggccgcttc acggaaagtt gttatatata agttcagtaa ataataatga aatataaatt    3120
ttaattatat ctagtactca ataagaagat ggagaaagtt atgttaatta tagttataaa    3180
ttatttataa atttaatata tatatataaa gaaatagtt gtataactaa taattatttt     3240
tacaatactt tatatagtta tatttaaaaa aattttaaaa ttaaaatact attattttgt    3300
tcaatatatt aatatttata ttatttaatt tattattgaa tatgaataaa ttttttttga    3360
aaattatatt tttaattttt agaaatttta tataactttc catatatata tttctgattt    3420
gtcaatttct tttgagattt atctaaattg atttgaattt ttttatttt taaaaaataa     3480 aataatttta aaatttcttg gaatttata taaattttg gatttttcaa aaaaaattga      3540 gattttttc ttttttttcg atttttaaa tttatttcag gaaaatataa actaactttt      3600
ctttgctttg ggtataatta atattagata acccacaaat tagatcaata ggagcttcat    3660
gtcctaatcc catttaatta cttttgttgt atcattaatt tagtcgacct tacatagtag    3720
ctctatgggg caaatagtta taatgttaa attagtattt aaatcttgaa gtttttaatt     3780
taaagttcag actattagta ttatatcaaa tatttaaggg taaatatata ttctaatatc    3840
taagcttggg tcaaggttta aattaagtac ttaaacttgg ttttatagtt caaattgatt    3900
taaataacta agtattaatt tgaattaaga agcaaagttc aagtacctaa ttagactata    3960
aaaaaaactt ttgctagtaa attgaaccct aaagtcgagt ttagttatct aattggacaa    4020
aaaaatctta ataccaatt taaaccctaa agtcaagttt aggtaccaaa gtgtatattt     4080
atctaatatt taaatttgat ccacctaatt taaattttt tggtccaatg caataagaga    4140
attaattaat acttacacac atgatagaga tatcccaca acagatacac actacaaaaa    4200
acattaaaaa atagaaagat atatttccta caaaatttaa aagcatttaa ttttttaact    4260
aacattagac aaatggaaat ggaaagactt atttttaagt ttatggatga atctaattta    4320
tctaaacatt gggttttttt ttttgtgac gaaatatggg tgagagaagg tagtaagcta     4380
agtaggggag taatatctca acaaataat taaaaaactc ctttaaatgt ggctataaat     4440
acctgaaacc aatccttctt tcctcaactc aaatcttcaa tctttagatc atctctccaa    4500
aaaaatacca tgtgcggaat tgttggcgca atagcacaaa gggacgtagc agaaatcctt    4560
cttgaaggac tccgtcgtct ggaatacaga ggatatgatt ctgccggtct agccgttgta    4620
gatgccgaag gtcacatgac acgtctaaga cgtctgggta aggttcaaat gctggctcaa    4680
gcagccgaag aacatccttt acatggtggc acaggtattg ctcacactag atgggctact    4740
cacggtgaac cttcagaggt aaatgctcat ccacatgtct ctgagcacat tgtggtcgtt    4800
cacaacggga tcatcgaaaa ccatgaacca cttcgagaag agctgaaagc tcgtggctat    4860
actttcgttt cagagacaga cactgaggtg attgctcatc tcgtgaactg ggaactgaaa    4920
caagggggaa ctctgagaga ggctgttcta cgtgctatcc ctcaattacg tggtgcttac    4980
gggacagtga tcatggattc aagacaccca gatacactgc tggcagcaag gtctggtagt    5040
ccactggtga ttggactggg gatgggagaa aactttatcg cttcggatca actggctctg    5100
ttacctgtga cacggagatt tatcttcctt gaagagggcg atatcgcgga ataactcga     5160 cgtagcgtaa acatcttcga taaaccgga gcagaagtaa aacgccagga tatcgaatcc    5220
aatcttcaat acgacgccgg cgataaaggc atataccgac actacatgca gaaagagatc    5280
tacgagcaac cgaacgctat caagaatacc cttactgggc gtatctcaca tggtcaggtt    5340
gacttatctg aactgggacc aaacgcagac gaactactgt cgaaggtaga acatattcag    5400
```

-continued

```
atcctcgcgt gtggtacttc ttataactct ggtatggtca gtcgctattg gtttgaatca    5460
ctggcaggaa ttccttgcga cgtcgaaatt gcctcggaat tcagatatcg caagtctgca    5520
gtaagacgca acagcctgat gataacgtta tctcagtctg gagaaacggc tgatacactg    5580
gctggattac gtctgtcaaa agagcttggc taccttggtt ctctagcaat ctgtaacgtt    5640
cctggtagct ctcttgtgcg agaatctgat cttgctctta tgactaacgc tggtacagaa    5700
atcggggtgg catccacaaa agcatttaca actcaactta cggtgctgct aatgcttgtg    5760
gcaaagctgt ctagactcaa aggtctagat gcctccatcg agcatgatat cgttcatggt    5820
ctgcaagctc ttcctagccg aattgagcag atgctgtcac aagacaaaag gattgaagcc    5880
ctggcagaag atttctcaga caagcatcac gctttgtttc cggtcgtgg cgatcagtat    5940 cctatcgctc tcgaaggcgc attgaagctc aaagagatct cctatataca cgctgaagct    6000
tacgctgcag gcgaactgaa acacggacct ctagctctta ttgacgcaga tatgcccgtt    6060
atcgtcgttg caccaaacaa cgaattgctg gagaagctga atcaaatat tgaagaggta    6120 cgtgcaagag gcggacaact ttatgtcttc gctgagcaag atgccggttt tgtaagtagc    6180
gataacatgc acatcatcga gatgcctcac gtggaagagg tgattgctcc gatcttctac    6240
acagttcccc tgcagcttct ggcttatcac gttgcccttt tcaaaggaac tgacgttgac    6300
cagccaagga atctcgcaaa gtcagtaacg gttgagtaaa cgcgtggcgc gcccccgatc    6360
cgcgtttgtg ttttctgggt ttctcactta agcgtctgcg ttttactttt gtattgggtt    6420
tggcgtttag tagtttgcgg tagcgttctt gttatgtgta attacgcttt ttcttcttgc    6480
ttcagcagtt tcggttgaaa tataaatcga atcaagtttc actttatcag cgttgtttta    6540
aattttggca ttaaattggt gaaaattgct tcaattttgt atctaaatag aagagacaac    6600
atgaaattcg acttttgacc tcaaatcttc gaacatttat ttcctgatt t cacgatggat    6660 gaggataacg aaagggcggt tcctatgtcc gggaaagttc ccgtagaaga caatgagcaa    6720
agctactgaa acgcggacac gacgtcgcat tggtacggat atgagttaaa ccgactcaat    6780
tcctttatta agacataaac cgattttggt taaagtgtaa cagtgagctg atataaaacc    6840
gaaacaaacc ggtacaagtt tgattgagca acttgatgac aaacttcaga attttggtta    6900
ttgaatgaaa atcatagtct aatcgtaaaa aatgtacaga agaaaagcta gagcagaaca    6960
aagattctat attctggttc caatttatca tcgctttaac gtccctcaga tttgatcggg    7020
gaattcgata tcattaccct gttatcccta aagcttatta atgtttgtcg aggagaaata    7080
tgagtcgagg catggataca ctaagttccc ctgaagtgag catgatcttt gatgctgaga    7140
tgattcccag agcaagatag tttgtgctgc aagtgacaca attgtaatga aaccaccact    7200
caacgaattt acttgtggct ttgacatgtc gtgtgctctg tttgtatttg tgagtgccgg    7260
ttggtaatta tttttgttaa tgtgatttta aaacctctta tgtaaatagt tactttatct    7320
attgaagtgt gttcttgtgg tctatagttt ctcaaaggga aattaaaatg ttgacatccc    7380
atttacaatt gataacttgg tatacacaaa ctttgtaaat ttggtgatat ttatggtcga    7440
aagaaggcaa tacccattgt atgttccaat atcaatatca atacgataac ttgataatac    7500
taacatatga ttgtcattgt ttttccagta tcaatataca ttaagctact acaaaattag    7560
tataaatcac tatattataa atcttttcg gttgtaactt gtaattcgtg ggtttttaaa    7620
ataaaagcat gtgaaaattt tcaaataatg tgatggcgca attttatttt ccgagttcca    7680
aaatattgcc gcttcattac cctaatttgt ggcgccacat gtaaaacaaa agacgattct    7740
tagtggctat cactgccatc acgcggatca ctaatatgaa ccgtcgatta aaacagatcg    7800
```

```
acggtttata catcatttta ttgtacacac ggatcgatat ctcagccgtt agatttaata   7860
tgcgatctga ttgctcaaaa aatagactct ccgtctttgc ctataaaaac aatttcacat   7920
ctttctcacc caaatctact cttaaccgtt cttcttcttc tacagacatc aatttctctc   7980
gactctagag gatccaagct tatcgatttc gaacccctca ggcgaagaac aggtatgatt   8040
tgtttgtaat tagatcaggg gtttaggtct ttccattact tttaatgtt tttctgtta   8100
ctgtctccgc gatctgattt tacgacaata gagtttcggg ttttgtccca ttccagtttg   8160
aaaataaagg tccgtctttt aagtttgctg gatcgataaa cctgtgaaga ttgagtctag   8220
tcgatttatt ggatgatcca ttcttcatcg ttttttttctt gcttcgaagt tctgtataac   8280
cagatttgtc tgtgtgcgat tgtcattacc tagccgtgta tcgagaacta gggttttcga   8340
gtcaattttg ccccttttgg ttatatctgg ttcgataacg attcatctgg attagggttt   8400
taagtggtga cgtttagtat tccaatttct tcaaaattta gttatggata atgaaaatcc   8460
ccaattgact gttcaatttc ttgttaaatg cgcagatcac aatggcttcg atctcctcct   8520
cagtcgcgac cgttagccgg accgcccctg ctcaggccaa catggtggct ccgttcaccg   8580
gccttaagtc caacgccgcc ttccccacca ccaagaaggc taacgacttc tccacccttc   8640
ccagcaacgg tggaagagtt caatgtatgc aggtgtggcc ggcctacggc aacaagaagt   8700
tcgagacgct gtcgtacctg ccgccgctgt ctatggcgcc caccgtgatg atggcctcgt   8760
cggccaccgc cgtcgctccg ttccaggggc tcaagtccac cgccagcctc cccgtcgccc   8820
gccgctcctc cagaagcctc ggcaacgtca gcaacggcgg aaggatccgg tgcatggccg   8880
gcgccgagga gatcgtgctg cagcccatca aggagatctc cggcaccgtc aagctgccgg   8940
ggtccaagtc gctttccaac cggatcctcc tactcgccgc cctgtccgag ggacaacag   9000
tggttgataa cctgctgaac agtgaggatg tccactacat gctcgggggcc ttgaggactc   9060
ttggtctctc tgtcgaagcg gacaaagctg ccaaaagagc tgtagttgtt ggctgtggtg   9120
gaaagttccc agttgaggat gctaaagagg aagtgcagct cttcttgggg aatgctggaa   9180
tcgcaatgcg gtccttgaca gcagctgtta ctgctgctgg tggaaatgca acttacgtgc   9240
ttgatggagt accaagaatg agggagagac ccattggcga cttggttgtc ggattgaagc   9300
agcttggtgc agatgttgat tgtttccttg gcactgactg cccacctgtt cgtgtcaatg   9360
gaatcggagg gctacctggt ggcaaggtca agctgtctgg ctccatcagc agtcagtact   9420
tgagtgcctt gctgatggct gctccttttgg ctcttgggga tgtggagatt gaaatcattg   9480
ataaattaat ctccattccg tacgtcgaaa tgacattgag attgatggag cgttttggtg   9540
tgaaagcaga gcattctgat agctgggaca gattctacat taagggaggt caaaaataca   9600
agtcccctaa aaatgcctat gttgaaggtg atgcctcaag cgcaagctat tcttggctg   9660
gtgctgcaat tactggaggg actgtgactg tggaaggttg tggcaccacc agtttgcagg   9720
gtgatgtgaa gtttgctgag gtactggaga tgatgggagc gaaggttaca tggaccgaga   9780
ctagcgtaac tgttactggc ccaccgcggg agccatttgg gaggaaacac ctcaaggcga   9840
ttgatgtcaa catgaacaag atgcctgatc tcgccatgac tcttgctgtg gttgccctct   9900
ttgccgatgg cccgacagcc atcagagacg tggcttcctg gagagtaaag gagaccgaga   9960
ggatggttgc gatccggacg gagctaacca agctgggagc atctgttgag gaagggccgg  10020
actactgcat catcacgccg ccggagaagc tgaacgtgac ggcgatcgac acgtacgacg  10080
accacaggat ggcgatggct ttctcccttg ccgcctgtgc cgaggtcccc gtcaccatcc  10140
```

```
gggaccctgg gtgcacccgg aagaccttcc ccgactactt cgatgtgctg agcactttcg    10200
tcaagaatta agctctagaa ctagtggatc ccccgatccg cgtttgtgtt ttctgggttt    10260
ctcacttaag cgtctgcgtt ttacttttgt attgggtttg gcgtttagta gtttgcggta    10320
gcgttcttgt tatgtgtaat tacgcttttt cttcttgctt cagcagtttc ggttgaaata    10380
taaatcgaat caagtttcac tttatcagcg ttgttttaaa ttttggcatt aaattggtga    10440
aaattgcttc aattttgtat ctaaatagaa gagacaacat gaaattcgac ttttgacctc    10500
aaatcttcga acatttattt cctgatttca cgatggatga ggataacgaa agggcggttc    10560
ctatgtccgg gaaagttccc gtagaagaca atgagcaaag ctactgaaac gcggacacga    10620
cgtcgcattg gtacggatat gagttaaacc gactcaattc ctttattaag acataaaccg    10680
attttggtta aagtgtaaca gtgagctgat ataaaaccga aacaaaccgg tacaagtttg    10740
attgagcaac ttgatgacaa acttcagaat tttggttatt gaatgaaaat catagtctaa    10800
tcgtaaaaaa tgtacagaag aaaagctaga gcagaacaaa gattctatat tctggttcca    10860
atttatcatc gctttaacgt ccctcagatt tgatcgggaa accaaaacgt cgtgagacag    10920
tttggttaac tataacggtc ctaaggtagc gatcgaggca ttacggcatt acggcactcg    10980
cgagggtccg aattcgagca tggagccatt tacaattgaa tatatcctgc cg           11032

<210> SEQ ID NO 4
<211> LENGTH: 11020
<212> TYPE: DNA
<213> ORGANISM: Artificial
<220> FEATURE:
<223> OTHER INFORMATION: T-DNA of pTDBI 250

<400> SEQUENCE: 4
aattacaacg gtatatatcc tgccagtact gggcccctc gagggcgatc gcgcggccgc       60
atgattagtt agatcaagct tttgagtctt caaaaacata aaaattacaa aaaaaaaaca      120
aacttaaaat catttatcaa tttgaacaac aaagcttggc cgaatgctaa gagcttaaaa      180
atggcttctt ttgtttcttt ttgttgcaaa cggtggagag aagagggaaa tgaagattga      240
ccatattttt ttattatgtt ttaacatata atattaataa tttaatcata attatacttt      300
ggtgaatgtg acagtgggga gatacgtaaa gtatataaca ttatactttt tgcaagcagt      360
tggctggtct acccaagagt gatcaaagtt tgagctgcct tcaatgagcc aatttttgcc      420
cataatggat aaaggcaatt tgtttagttc aactgctcac agaataatgt taaaatgaaa      480
ttaaaataag gtggcctggt cacacacaca aaaaaaaact aatgttggtt ggttgaattt      540
tatattacgg aatgtaatat tatatttaa aataaaatta tgttatttag attcttaata       600
ttttgagcat tccatactat aatttcgtat acataatatt aaaatatagt aatataaagt      660
gtaattaact ttaaattaca agcataatat taaattttga atcaattaat ttttatttct      720
attattttaa ttaatttagt ctattttttc aaaataaaat ttaaatctaa ataaaaataa      780
ttttccctta atgttgaaac aactcatgtt atacttcaaa attataagta ttatatttac      840
cttgatgatt tatttattag tatattaatt ctgattataa ttatggtggg atacaatcgc      900
tttccactaa atattttaac tatgatttat aaatttattt caacatcgta tatttactta      960
ttaatacata atttatcata atttatggaa aattgagacc aagaaacatt aagagaacaa     1020
attctataac aaagacaatt tagaaaaaaa tgtactttta ggtaattta agtactctta      1080 accaaacaca aaaattcaaa tcaaatgaac taaataagat aatataacat acggaacatc     1140
ttacttgtaa tcttacattc ccataatttt attatgaaaa ataatcttat attactcgaa     1200
```

```
ctaaatgttg tcacaaatta ttatctaaat aaagaaaaac acttaatttt tataacattt    1260
tttcatatat ttgaaagatt atattttgta tatttacgta aaaatatttg acatagattg    1320
agcaccttct taacataatc ccaccataag tcaagtatgt agatgagaaa ttggtacaaa    1380
caacgtgggg ccaaatccca ccaaaccatc tctcattctc tcctataaaa ggcttgctac    1440
acatagacaa caatccacac acaaatacac gttctttttct ttctatttga ttaaccatga   1500
gtaaacggaa tccgaagatt ctgaagattt ttctgtatat gttacttctc aactctctct    1560
ttctcatcat ctacttcgtt tttcactcat cgtcgttttc aagtgtcgta gatgtgatcg    1620
gtttgcttgc gactgcagcc tacgtgacgt tggcgagcgc atacaaggtg gtccagttca    1680
ttaacgtgtc gagcgtaacg gatgtcgctg gtctcgaaag tgatgctttg ccgctcactc    1740
caagggttga cgttatcgtg ccgacattca atgagaactc cagcacattg ctcgagtgcg    1800
tcgcttctat atgcgcacaa gactaccgcg gaccaataac gattgtcgtg gtagacgatg    1860
ggtcgaccaa caaacatca tttcacgcag tatgcgacaa gtacgcgagc gacgaaaggt     1920
tcatatttgt cgaacttgat caaaacaagg ggaagcgcgc gcgcaaatg gaggccatca     1980 ggagaacaga cggagacctg atactaaacg tagactcgga cacggttata gataaggatg    2040
ttgttacaaa gcttgcgtcg tccatgagag ccccgaatgt cggtggtgtc atgggcagc     2100 tcgttgcaaa gaatcgagaa agatcttggc ttaccagatt aatcgatatg gagtactggc    2160
ttgcgtgtaa cgaggagcgc attgcgcagt cgaggtttgg ctccgtgatg tgttgttgtg    2220
ggccgtgcgc catgtataga agatctgcaa ttacgccact attggcagaa tatgagcacc    2280
agacattcct agggcgtccg agcaactttg gtgaggatcg ccatctcaca atcctgatgc    2340
tgaaggcggg atttcggacc gggtacgtcc caggtgccgt agcgaggacg ttggttccgg    2400
atgggctggc gccgtacctg cgccagcaac tccgctgggc ccgcagcact tatcgcgaca    2460
ccgccctcgc cttacgtata aagaaaaatc taagcaaata tatcacctttt gagatatgcg   2520 cacagaattt gggtacggct ctcttacttg tgatgaccat gatttcgctt tcgctgacta    2580
catcagggtc gcaaacgccc gttatcattc tgggtgtcgt tgtggggatg tctataataa    2640
gatgttgttc tgtcgcccctt atagcgaaag attttcggtt tctatacttc atcgttcact   2700
cagcgttgaa tgttctaatt ttaacgccgt taaaactcta tgccctgtta accattcggg    2760
atagtcggtg gctatcacgc gagagttcct aagctagcaa gcttggacac gctgaaatca    2820
ccagtctctc tctacaaatc tatctctctc tattttctcc ataataatgt gtgagtagtt    2880
cccagataag ggaattaggg ttcctatagg gtttcgctca tgtgttgagc ataagaaa     2940 cccttagtat gtatttgtat ttgtaaaata cttctatcaa taaaatttct aattcctaaa    3000
accaaaatcc agtactaaaa tccagacgcg tcctgcaggc ccgggttaat taagcggccg    3060
catgattagt tagatcaagc ttttgagtct tcaaaaacat aaaaattaca aaaaaaaaac    3120
aaacttaaaa tcatttatca atttgaacaa caaagcttgg ccgaatgcta agagcttaaa    3180
aatggcttct tttgtttctt tttgttgcaa acggtggaga gaagagggaa atgaagattg    3240
accatatttt tttattatgt tttaacatat aatattaata atttaatcat aattatactt    3300
tggtgaatgt gacagtgggg agatacgtaa agtatataac attatacttt ttgcaagcag    3360
ttggctggtc tacccaagag tgatcaaagt ttgagctgcc ttcaatgagc caattttttgc   3420 ccataatgga taaaggcaat ttgtttagtt caactgctca cagaataatg ttaaaatgaa    3480
attaaaataa ggtggcctgg tcacacacac aaaaaaaaac taatgttggt tggttgaatt    3540
```

-continued

```
ttatattacg gaatgtaata ttatatttta aaataaaatt atgttattta gattcttaat    3600
attttgagca ttccatacta taatttcgta tacataatat taaaatatag taatataaag    3660
tgtaattaac tttaaattac aagcataata ttaaattttg aatcaattaa tttttatttc    3720
tattatttta attaatttag tctattttt caaaataaaa tttaaatcta aataaaaata    3780
attttccctt aatgttgaaa caactcatgt tatacttcaa aattataagt attatattta    3840
ccttgatgat ttatttatta gtatattaat tctgattata attatggtgg gatacaatcg    3900
ctttccacta aatattttaa ctatgattta taaatttatt tcaacatcgt atatttactt    3960
attaatacat aatttatcat aatttttatgg aaattgagac caagaaacat taagagaaca    4020
aattctataa caaagacaat ttagaaaaaa atgtactttt aggtaatttt aagtactctt    4080
aaccaaacac aaaaattcaa atcaaatgaa ctaaataaga taatataaca tacgaaacat    4140
cttacttgta atcttacatt cccataattt tattatgaaa aataatctta tattactcga    4200
actaaatgtt gtcacaaatt attatctaaa taaagaaaaa cacttaattt ttataacatt    4260
ttttcatata tttgaaagat tatattttgt atatttacgt aaaaatattt gacatagatt    4320
gagcaccttc ttaacataat cccaccataa gtcaagtatg tagatgagaa attggtacaa    4380
acaacgtggg gccaaatccc accaaaccat ctctcattct ctcctataaa aggcttgcta    4440
cacatagaca acaatccaca cacaaataca cgttcttttc tttctatttg attaaccatg    4500
tgcggaattg ttggcgcaat agcacaaagg gacgtagcag aaatccttct gaaggactc     4560
cgtcgtctgg aatacagagg atatgattct gccggtctag ccgttgtaga tgccgaaggt    4620
cacatgacac gtctaagacg tctgggtaag gttcaaatgc tggctcaagc agccgaagaa    4680
catcctttac atggtggcac aggtattgct cacactagat gggctactca cggtgaacct    4740
tcagaggtaa atgctcatcc acatgtctct gagcacattg tggtcgttca caacgggatc    4800
atcgaaaacc atgaaccact tcgagaagag ctgaaagctc gtggctatac tttcgtttca    4860
gagacagaca ctgaggtgat tgctcatctc gtgaactggg aactgaaaca agggggaact    4920
ctgagagagg ctgttctacg tgctatccct caattacgtg gtgcttacgg gacagtgatc    4980
atggattcaa gacacccaga tacactgctg gcagcaaggt ctggtagtcc actggtgatt    5040
ggactgggga tgggagaaaa ctttatcgct tcggatcaac tggctctgtt acctgtgaca    5100
cggagattta tcttccttga agagggcgat atcgcggaaa taactcgacg tagcgtaaac    5160
atcttcgata aaaccggagc agaagtaaaa cgccaggata tcgaatccaa tcttcaatac    5220
gacgccggcg ataaaggcat ataccgcacac tacatgcaga aagagatcta cgagcaaccg    5280
aacgctatca agaataccct tactgggcgt atctcacatg gtcaggttga cttatctgaa    5340
ctgggaccaa acgcagacga actactgtcg aaggtagaac atattcagat cctcgcgtgt    5400
ggtacttctt ataactctgg tatggtcagt cgctattggt ttgaatcact ggcaggaatt    5460
ccttgcgacg tcgaaattgc ctcggaattc agatatcgca agtctgcagt aagacgcaac    5520
agcctgatga taacgttatc tcagtctgga gaaacggctg atacactggc tggattacgt    5580
ctgtcaaaag agcttggcta ccttggttct ctagcaatct gtaacgttcc tggtagctct    5640
cttgtgcgag aatctgatct tgctcttatg actaacgctg gtacagaaat cggggtggca    5700
tccacaaaag catttacaac tcaacttacg gtgctgctaa tgcttgtggc aaagctgtct    5760
agactcaaag gtctagatgc ctccatcgag catgatatcg ttcatggtct gcaagctctt    5820
cctagccgaa ttgagcagat gctgtcacaa gacaaaagga ttgaagccct ggcagaagat    5880
ttctcagaca agcatcacgc tttgtttctc ggtcgtggcg atcagtatcc tatcgctctc    5940
```

```
gaaggcgcat tgaagctcaa agagatctcc tatatacacg ctgaagctta cgctgcaggc    6000
gaactgaaac acggacctct agctcttatt gacgcagata tgcccgttat cgtcgttgca    6060
ccaaacaacg aattgctgga gaagctgaaa tcaaatattg aagaggtacg tgcaagaggc    6120
ggacaacttt atgtcttcgc tgagcaagat gccggttttg taagtagcga taacatgcac    6180
atcatcgaga tgcctcacgt ggaagaggtg attgctccga tcttctacac agttcccctg    6240
cagcttctgg cttatcacgt tgcccttatc aaaggaactg acgttgacca gccaaggaat    6300
ctcgcaaagt cagtaacggt tgagtaaacg cgtggcgcgc ccccgatccg cgtttgtgtt    6360
ttctgggttt ctcacttaag cgtctgcgtt ttacttttgt attgggtttg gcgtttagta    6420
gtttgcggta gcgttcttgt tatgtgtaat tacgcttttt cttcttgctt cagcagtttc    6480
ggttgaaata taaatcgaat caagtttcac tttatcagcg ttgttttaaa ttttggcatt    6540
aaattggtga aaattgcttc aattttgtat ctaaatagaa gagacaacat gaaattcgac    6600
ttttgacctc aaatcttcga acatttattt cctgatttca cgatggatga ggataacgaa    6660
agggcggttc ctatgtccgg gaaagttccc gtagaagaca atgagcaaag ctactgaaac    6720
gcggacacga cgtcgcattg gtacggatat gagttaaacc gactcaattc ctttattaag    6780
acataaaccg attttggtta aagtgtaaca gtgagctgat ataaaaccga acaaaccgg    6840 tacaagtttg attgagcaac ttgatgacaa acttcagaat tttggttatt gaatgaaaat    6900
catagtctaa tcgtaaaaaa tgtacagaag aaaagctaga gcagaacaaa gattctatat    6960
tctggttcca atttatcatc gctttaacgt ccctcagatt tgatcgggga attcgatatc    7020
attaccctgt tatccctaaa gcttattaat gtttgtcgag gagaaatatg agtcgaggca    7080
tggatacact aagttcccct gaagtgagca tgatctttga tgctgagatg attcccagag    7140
caagatagtt tgtgctgcaa gtgacacaat tgtaatgaaa ccaccactca acgaatttac    7200
ttgtggcttt gacatgtcgt gtgctctgtt tgtatttgtg agtgccggtt ggtaattatt    7260
tttgttaatg tgatttttaaa acctcttatg taaatagtta ctttatctat tgaagtgtgt    7320
tcttgtggtc tatagtttct caaagggaaa ttaaaatgtt gacatcccat ttacaattga    7380
taacttggta tacacaaact ttgtaaattt ggtgatattt atggtcgaaa gaaggcaata    7440
cccattgtat gttccaatat caatatcaat acgataactt gataatacta acatatgatt    7500
gtcattgttt ttccagtatc aatatacatt aagctactac aaaattagta taaatcacta    7560
tattataaat cttttcggt tgtaacttgt aattcgtggg ttttaaaat aaaagcatgt    7620 gaaaatttc aaataatgtg atggcgcaat tttattttcc gagttccaaa atattgccgc    7680
ttcattaccc taatttgtgg cgccacatgt aaaacaaaag acgattctta gtggctatca    7740
ctgccatcac gcgatcact aatatgaacc gtcgattaaa acagatcgac ggtttataca    7800
tcattttatt gtacacacgg atcgatatct cagccgttag atttaatatg cgatctgatt    7860
gctcaaaaaa tagactctcc gtctttgcct ataaaaacaa tttcacatct ttctcaccca    7920
aatctactct taaccgttct tcttcttcta cagacatcaa tttctctcga ctctagagga    7980
tccaagctta tcgatttcga acccctcagg cgaagaacag gtatgatttg tttgtaatta    8040 gatcagggg ttaggtcttt ccattacttt ttaatgtttt ttctgttact gtctccgcga    8100
tctgatttta cgacaataga gtttcgggtt ttgtcccatt ccagtttgaa aataaaggtc    8160 cgtctttta gtttgctgga tcgataaacc tgtgaagatt gagtctagtc gatttattgg    8220
atgatccatt cttcatcgtt tttttcttgc ttcgaagttc tgtataacca gatttgtctg    8280
```

```
tgtgcgattg tcattaccta gccgtgtatc gagaactagg gttttcgagt caattttgcc    8340
ccttttggtt atatctggtt cgataacgat tcatctggat tagggtttta agtggtgacg    8400
tttagtattc caatttcttc aaaatttagt tatggataat gaaaatcccc aattgactgt    8460
tcaatttctt gttaaatgcg cagatcacaa tggcttcgat ctcctcctca gtcgcgaccg    8520
ttagccggac cgcccctgct caggccaaca tggtggctcc gttcaccggc cttaagtcca    8580
acgccgcctt ccccaccacc aagaaggcta acgacttctc cacccttccc agcaacggtg    8640
gaagagttca atgtatgcag gtgtggccgg cctacggcaa caagaagttc gagacgctgt    8700
cgtacctgcc gccgctgtct atggcgccca ccgtgatgat ggcctcgtcg gccaccgccg    8760
tcgctccgtt ccaggggctc aagtccaccg ccagcctccc cgtcgcccgc cgctcctcca    8820
gaagcctcgg caacgtcagc aacggcggaa ggatccggtg catggccggc gccgaggaga    8880
tcgtgctgca gcccatcaag gagatctccg gcaccgtcaa gctgccgggg tccaagtcgc    8940
tttccaaccg gatcctccta ctcgccgccc tgtccgaggg gacaacagtg gttgataacc    9000
tgctgaacag tgaggatgtc cactacatgc tcggggcctt gaggactctt ggtctctctg    9060
tcgaagcgga caaagctgcc aaaagagctg tagttgttgg ctgtggtgga aagtttcccag   9120
ttgaggatgc taaagaggaa gtgcagctct tcttggggaa tgctggaatc gcaatgcggt    9180
ccttgacagc agctgttact gctgctggtg gaaatgcaac ttacgtgctt gatggagtac    9240
caagaatgag ggagagaccc attggcgact tggttgtcgg attgaagcag cttggtgcag    9300
atgttgattg tttccttggc actgactgcc cacctgttcg tgtcaatgga atcggagggc    9360
tacctggtgg caaggtcaag ctgtctggct ccatcagcag tcagtacttg agtgccttgc    9420
tgatggctgc tcctttggct cttggggatg tggagattga aatcattgat aaattaatct    9480
ccattccgta cgtcgaaatg acattgagat tgatggagcg ttttggtgtg aaagcagagc    9540
attctgatag ctgggacaga ttctacatta agggaggtca aaaatacaag tcccctaaaa    9600
atgcctatgt tgaaggtgat gcctcaagcg caagctattt cttggctggt gctgcaatta    9660
ctggagggac tgtgactgtg gaaggttgtg gcaccaccag tttgcagggt gatgtgaagt    9720
ttgctgaggt actggagatg atgggagcga aggttacatg gaccgagact agcgtaactg    9780
ttactggccc accgcgggag ccatttggga ggaaacacct caaggcgatt gatgtcaaca    9840
tgaacaagat gcctgatgtc gccatgactc ttgctgtggt tgccctcttt gccgatggcc    9900
cgacagccat cagagacgtg gcttcctgga gagtaaagga gaccgagagg atggttgcga    9960
tccggacgga gctaaccaag ctgggagcat ctgttgagga agggccggac tactgcatca   10020
tcacgccgcc ggagaagctg aacgtgacgg cgatcgacac gtacgacgac cacaggatgg   10080
cgatggcttt ctcccttgcc gcctgtgccg aggtccccgt caccatccgg gaccctgggt   10140
gcacccggaa gaccttcccc gactacttcg atgtgctgag cactttcgtc aagaattaag   10200
ctctagaact agtggatccc ccgatccgcg tttgtgtttt ctgggtttct cacttaagcg   10260
tctgcgtttt acttttgtat tgggtttggc gtttagtagt ttgcggtagc gttcttgtta   10320
tgtgtaatta cgcttttct tcttgcttca gcagtttcgg ttgaaatata atcgaatca    10380
agtttcactt tatcagcgtt gttttaaatt tggcattaa attggtgaaa attgcttcaa    10440
ttttgtatct aaatagaaga gacaacatga aattcgactt tgacctcaa atcttcgaac    10500
atttatttcc tgatttcacg atggatgagg ataacgaaag gcggttcct atgtccggaa    10560
aagttcccgt agaagacaat gagcaaagct actgaaacgc ggcacgacg tcgcattggt    10620
acggatatga gttaaaccga ctcaattcct ttattaagac ataaaccgat tttggttaaa    10680
```

```
gtgtaacagt gagctgatat aaaaccgaaa caaaccggta caagtttgat tgagcaactt   10740
gatgacaaac ttcagaattt tggttattga atgaaaatca tagtctaatc gtaaaaaatg   10800
tacagaagaa aagctagagc agaacaaaga ttctatattc tggttccaat ttatcatcgc   10860
tttaacgtcc ctcagatttg atcgggaaac caaaacgtcg tgagacagtt tggttaacta   10920
taacggtcct aaggtagcga tcgaggcatt acggcattac ggcactcgcg agggtccgaa   10980
ttcgagcatg gagccattta caattgaata tatcctgccg                         11020
```